(12) United States Patent
Sanderson

(10) Patent No.: US 7,695,692 B2
(45) Date of Patent: Apr. 13, 2010

(54) APPARATUS AND METHOD FOR PRODUCING CHLORINE DIOXIDE

(76) Inventor: William D. Sanderson, 2053 Fillmore St., #101, San Francisco, CA (US) 94123

( * ) Notice: Subject to any disclaimer, the term of this patent is extended or adjusted under 35 U.S.C. 154(b) by 1377 days.

(21) Appl. No.: 11/002,647

(22) Filed: Dec. 3, 2004

(65) Prior Publication Data

US 2005/0079124 A1    Apr. 14, 2005

Related U.S. Application Data

(63) Continuation-in-part of application No. PCT/US2004/025201, filed on Aug. 5, 2004.

(60) Provisional application No. 60/492,729, filed on Aug. 6, 2003.

(51) Int. Cl.
   *B01J 19/08*    (2006.01)
(52) U.S. Cl. .................................... 422/186.3
(58) Field of Classification Search ............... 422/186.3
   See application file for complete search history.

(56) References Cited

U.S. PATENT DOCUMENTS

| | | | |
|---|---|---|---|
| 3,726,062 A | 4/1973 | Hungate | |
| 3,804,329 A | 4/1974 | Martner | |
| 4,456,511 A | 6/1984 | Fisher | |
| 4,738,593 A | 4/1988 | Reifschneider | |
| 4,746,466 A | 5/1988 | Takahashi | |
| 4,846,856 A | 7/1989 | Burger | |
| 4,874,489 A | 10/1989 | Callerame | |
| 4,877,500 A | 10/1989 | Callerame | |
| 5,006,326 A | 4/1991 | Mayurnik | |
| 5,087,374 A * | 2/1992 | Ding ........................... | 210/673 |
| 5,091,166 A | 2/1992 | Engstrom | |
| 5,091,167 A | 2/1992 | Engstrom | |
| 5,110,580 A | 5/1992 | Rosenblatt | |
| 5,300,260 A | 4/1994 | Keshet | |
| 5,614,151 A | 3/1997 | LeVay | |
| 5,919,374 A | 7/1999 | Harvey | |
| 6,171,558 B1 | 1/2001 | Simpson | |
| 6,197,215 B1 | 3/2001 | Pitochelli | |
| 6,363,734 B1 | 4/2002 | Aoyagi | |
| 6,602,442 B1 | 8/2003 | Pitochelli | |
| 6,676,850 B2 | 1/2004 | Speronello | |
| 6,699,404 B2 | 3/2004 | Speronello | |
| 6,962,714 B2 | 11/2005 | Hei | |
| 7,087,190 B2 | 8/2006 | Hei | |

(Continued)

FOREIGN PATENT DOCUMENTS

EP    0414893    3/1991

(Continued)

OTHER PUBLICATIONS

Cosson, et. al., "Photodeposition of Chlorine Dioxide and Sodium Chlorite in Aqueous Solution by Irradiation with Ultraviolet Light," In. Eng. Chem. Res. 1994, 33, pp. 1468-1475.

*Primary Examiner*—Kishor Mayekar
(74) *Attorney, Agent, or Firm*—Jeffrey S. Melcher; Manelli Denison & Selter PLLC

(57) ABSTRACT

Provided are apparatuses and methods for making chlorine dioxide on demand by converting a chlorine dioxide generating solution into chlorine dioxide by exposure to UV light.

10 Claims, 16 Drawing Sheets

U.S. PATENT DOCUMENTS

| | | |
|---|---|---|
| 7,118,852 B2 * | 10/2006 | Purdum .................. 435/2 |
| 2002/0192110 A1 | 12/2002 | Barlick |
| 2003/0127535 A1 | 7/2003 | Adiga |
| 2003/0152619 A1 | 8/2003 | Stevens |
| 2003/0180384 A1 | 9/2003 | Koermer |
| 2004/0022675 A1 | 2/2004 | An |
| 2004/0035803 A1 | 2/2004 | Cronan |
| 2004/0135116 A1 | 7/2004 | Speronello |
| 2005/0013878 A1 | 1/2005 | Mingzhong |
| 2005/0072308 A1 | 4/2005 | Aoyagi |
| 2005/0079124 A1 | 4/2005 | Sanderson |
| 2005/0155936 A1 | 7/2005 | Martin |
| 2005/0249658 A1 | 11/2005 | Tarbet |
| 2006/0013751 A1 | 1/2006 | Martin |
| 2006/0016765 A1 | 1/2006 | DiPietro |
| 2006/0018940 A1 | 1/2006 | DiPietro |
| 2006/0115388 A1 | 6/2006 | Sanderson |
| 2006/0197058 A1 | 9/2006 | Martin |

FOREIGN PATENT DOCUMENTS

| | | |
|---|---|---|
| EP | 0581550 | 12/1997 |
| JP | 02261514 | 10/1990 |
| JP | 11207124 | 8/1999 |
| JP | 2000161727 | 6/2000 |
| JP | 2000202227 | 7/2000 |
| JP | 2000202333 | 7/2000 |
| JP | 2001033070 | 2/2001 |
| WO | 03055797 | 7/2003 |
| WO | 2004089081 | 4/2004 |
| WO | 2004054685 | 7/2004 |
| WO | 2005016011 | 2/2005 |
| WO | 2006020247 | 2/2006 |
| WO | 2006060563 | 6/2006 |
| WO | 2007078838 | 7/2007 |
| WO | 2007149906 | 12/2007 |

* cited by examiner

APPARATUS AND METHOD FOR PRODUCING CHLORINE DIOXIDE

This application is a Continuation-in-Part of PCT/US2004/025201, filed Aug. 5, 2004, which claims priority to U.S. Provisional Patent Application Ser. No. 60/492,729, filed Aug. 6, 2003, the complete disclosures of which are incorporated herein by reference.

1. FIELD OF THE INVENTION

The present invention relates to an apparatus and method for production of chlorine dioxide from readily available raw materials. More specifically, the invention relates to an apparatus and method for converting a chlorine dioxide generating solution into chlorine dioxide on demand by exposure to UV light.

2. BACKGROUND OF THE INVENTION

Chlorine dioxide enjoys considerable commercial and industrial importance in a wide variety of applications. It is currently used in large quantities as a bleaching agent for wood pulp, paper, fats, oils, tallow, and flour.

A recent series of regulatory approvals have increased the use of chlorine dioxide as a disinfectant and sanitizer in the food processing industry. New federal guidelines have permitted its use in meat, dairy, poultry, fruit and vegetable post-harvest produce, and prepared foodstuffs. In most circumstances, chlorine dioxide does not cause organoleptic impairments of food products.

Chlorine dioxide is also widely used in the wastewater industry both as a pollution control agent and a potable water treatment. Chlorine dioxide is an excellent sulfide scavenging agent and is employed in scrubbing towers in wastewater, rendering, and the oil and gas industry.

The unique properties of chlorine dioxide provide a growing receptivity in its use as an environmental and microbial control agent. Chlorine dioxide reacts with a high degree of specificity towards certain industrial pollutants, such as sulfides, amines, mercaptans, and cyanide while not reacting with ammonia or most organic compounds.

The highly selective nature of chlorine dioxide is important in disinfection. Unwanted disinfection by-products such as trihalomethanes (THMs) and polychlorobiphenyls (PCBs) are not formed as they are with chlorine or hypochlorites. Chlorine dioxide also is effective over a wide pH range, does not disassociate in solutions, has rapid disinfection kinetics, and does not accumulate in treated solutions.

Chlorine dioxide is most often generated on-site due to prohibition and hazards of its transport and storage. It has been produced conventionally by several chemical and electrochemical processes. The most common means of production is the acidification of aqueous sodium chlorite. Strong acids such as sulfuric or hydrochloric give high yields of chlorine dioxide while weaker (and safer) acids such as citric and lactic give much lower yields.

The acidic conversion of chlorite to chlorine dioxide is greatly enhanced in yield by adding a chlorine donor such as hypochlorite or chlorine gas. While advantageous in recoverable yield, a three-precursor system introduces a greater level of complexity in apparatus and reactor design. Current methods for producing chlorine dioxide gas employ highly toxic chlorine gas. On-site storage of hypochlorites, strong acids, and chlorine gas also poses additional hazards and regulatory scrutiny to the end user.

Electrochemical generators have attempted to partially address this issue. Such generators utilize a singe precursor, normally sodium chlorite or sodium chlorate. The produced chlorine dioxide product is separated from the electrolyte solution using a gas permeable structure. However, they are not widely used due to other disadvantages such as high cost, generation of explosive hydrogen gas, and reliability. New designs have begun to address these concerns A potentially superior and alternative method for producing chlorine dioxide is by photochemical oxidation. Photochemical reactions of chlorine dioxide and oxyanions of chlorine have been reported by E. J. Brown and M. Cheung (1932) and disclosed in U.S. Pat. Nos. 2,043,284, 2,457,285, and 2,683,651.

More recent work of photochemical methods is disclosed in U.S. Pat. Nos. 4,414,180 and 4,456,511 to Fisher. This work describes a generator containing aqueous sodium chlorite illuminated by externally placed incandescent fluorescent bulbs. The sodium chlorite is photochemically oxidized to chlorine dioxide and removed from the aqueous solution with a gaseous nitrogen or air stream.

Further, more detailed work is disclosed in U.S. Pat. No. 4,874,489 to J. Callerame, which describes a tubular chamber containing sodium chlorite. An ultraviolet source, namely a low pressure mercury vapor bulb, was housed inside the vessel and the inside wall was made from a UV reflector such as polished aluminum. The reaction was discontinued when the chlorine dioxide concentration reached ten percent weight and the entire reaction product was removed from the reaction space. Ten percent was the upper limit chosen due to explosive properties of chlorine dioxide.

Similarly in U.S. Pat. No. 4,877,500 to Callerame, mixtures of chlorine and oxygen gas and aqueous solutions of sodium hypochlorite were photochemically converted to chlorine dioxide. As in the earlier Callerame patent, the solution was held within the tubular vessel until the maximum concentration of chlorine dioxide reached ten percent. Afterwards, the entire reaction contents containing chlorine dioxide were removed and conveyed to their place of use. In the photochemical reactions of chlorine and oxygen, explosions were reported to have occurred in two instances.

Improvements in safety of photochemical methods were reported by Simpson in U.S. Pat. No. 6,171,558. A means is described for positioning a UV bulb in a container of aqueous chlorite. The aqueous chlorite is circulated through a circulation tube by an air or gas sparge. This also effectively removes chlorine dioxide and thus reduces the safety hazardous associated with its accumulation in solution.

While considerably improving upon the safety of the prior photochemical methods the following limitations are still imposed:

(1) The prior art requires additional air moving system to generate a gas sparge.
(2) The prior art was conducted in fragile quartz tubes and aspirators.
(3) The prior art requires a circulation tube in proximity to the ultraviolet bulb to conduct the chlorite precursor across the field of ultraviolet radiation.
(4) The prior art production of chlorine dioxide cannot be directly regulated by controlled addition of chlorite precursor. The prior art production of chlorine dioxide must be controlled by bulb intensity and gas sparge rate.
(5) The scale-up of the prior art device is difficult. The chlorine dioxide production rate also decreases as the chlorite is exhausted Chlorine dioxide has the potential for increased use in a variety of commercial and industrial applications. The apparatus for its generation would ideally be safe, economical, easy-to-use, and not require storage of hazardous ingredients. A clear and compelling need exists for a device that produces chlorine dioxide while fulfilling the above criteria.

SUMMARY OF THE INVENTION

Objectives of the present invention include providing apparatuses and methods for generating chlorine dioxide in an air stream or dissolved in a liquid stream on demand that solve the numerous problems of the prior art described herein above.

The objectives of the present invention are met by a chlorine dioxide generator comprising:

a reaction vessel constructed and arranged to contain a chlorine dioxide generating solution that forms an activated solution containing chlorine dioxide upon exposure to UV light;

a source of UV light constructed and arranged to provide UV light to said reaction vessel such that when said generator is operating UV light contacts the chlorine dioxide generating solution when present within the reaction vessel to produce the activated solution containing chlorine dioxide;

at least one solution inlet associated with said reaction vessel constructed and arranged to allow chlorine dioxide generating solution to flow into said reaction vessel during operation of said generator;

at least one solution outlet associated with said reaction vessel constructed and arranged to allow spent activated solution to flow out of said reaction vessel during operation of said generator;

at least one chlorine dioxide exit associated with said reaction vessel constructed and arranged to allow chlorine dioxide gas to exit said reaction vessel during operation of said generator;

a gas permeable structure constructed and arranged to allow chlorine dioxide gas to exit said reaction vessel during operation of said generator by passing through said structure and to contain the chlorine dioxide generating solution and activated solution in said reaction vessel when present in the reaction vessel;

a source of ultrasonic vibrations constructed and arranged to vibrate the activated solution and facilitate removal of chlorine dioxide from the activated solution during operation of said generator; and evacuating structure in communication with the reaction vessel to facilitate continuous evacuation of chlorine dioxide from said reaction vessel during operation of said generator.

The objectives of the invention are also met by a method of making chlorine dioxide on demand comprising:

exposing a chlorine dioxide generating solution to UV light to form an activated solution containing chlorine dioxide in a reaction vessel;

agitating said activated solution using a source of ultrasonic vibrations to drive chlorine dioxide from said activated solution;

using a gas permeable structure to separate said chlorine dioxide from said activated solution;

facilitating the evacuation of chlorine dioxide from the reaction vessel using reduced pressure from a water driven eductor or air flow; and forming an air flow stream containing chlorine dioxide or an aqueous stream containing dissolved chlorine dioxide.

The objectives of the invention are met by a chlorine dioxide generator and air cleanser comprising:

a reaction vessel constructed and arranged to contain a chlorine dioxide generating solution that forms an activated solution containing chlorine dioxide upon exposure to UV light;

a source of UV light constructed and arranged to provide UV light to said reaction vessel such that when said generator is operating UV light contacts the chlorine dioxide generating solution when present within the reaction vessel to produce the activated solution containing chlorine dioxide;

a column in communication with said reaction vessel having at least one air inlet and at least one air outlet;

dispersing structure in communication with said column for dispersing activated solution in said column during operation;

a pump for transferring activated solution from said reaction vessel to said dispersing structure;

at least one liquid outlet in said column constructed and arranged to allow activated liquid leaving the column during operation to transfer back to said reaction vessel; and a air-moving device to provide an air stream through said column.

The objectives of the invention are further met by a chlorine dioxide generator for providing a stream of chlorine dioxide dissolved in a liquid solvent comprising:

a reaction vessel constructed and arranged to contain a chlorine dioxide generating solution that forms an activated solution containing chlorine dioxide upon exposure to UV light having at least one vessel air inlet and at least one vessel air outlet;

a source of UV light constructed and arranged to provide UV light to said reaction vessel such that when said generator is operating UV light contacts the chlorine dioxide generating solution when present within the reaction vessel to produce the activated solution containing chlorine dioxide;

a source of ultrasonic vibrations constructed and arranged to vibrate the activated solution and facilitate removal of chlorine dioxide from the activated solution during operation of said generator;

a column in communication with said reaction vessel having at least one column air inlet, at least one column air outlet, at least one liquid input and at least one liquid outlet;

a air-moving device in communication with the vessel air inlet to provide an air stream through said reaction vessel during operation to form an air stream containing chlorine dioxide, the vessel air outlet being in communication with the column air inlet;

dispersing structure in communication with said liquid inlet for dispersing solvent in said column such that the solvent contacts the air stream containing chlorine dioxide during operation to form solvent containing dissolved chlorine dioxide; and at least one liquid outlet in said column constructed and arranged to allow solvent containing dissolved chlorine dioxide to exit the column during operation.

The objectives of the invention are also met by a method of cleaning an air stream comprising:

exposing a chlorine dioxide generating solution to UV light to form an activated solution containing chlorine dioxide in a reaction vessel;

transferring the activated solution to a column in communication with said reaction vessel; and flowing an air stream through said column to contact said activated solution and form a cleaned air stream leaving said column.

The objectives of the invention are further met by a method of providing a liquid stream of chlorine dioxide comprising:
exposing a chlorine dioxide generating solution to UV light to form an activated solution containing chlorine dioxide in a reaction vessel;
agitating said activated solution using a source of ultrasonic vibrations to drive chlorine dioxide from said activated solution;
flowing an air stream through said vessel to form an air stream containing chlorine dioxide;

transferring the air stream containing chlorine dioxide to a column in communication with said reaction vessel; and supplying a solvent into said column such that it contacts the air stream containing chlorine dioxide to form a solvent containing chlorine dioxide.

The objectives of the invention are also met by an air cleanser comprising:

an activation vessel constructed and arranged to contain a chlorine dioxide generating solution that forms an activated solution containing chlorine dioxide upon exposure to UV light;

a source of UV light constructed and arranged to provide UV light to said activation vessel such that when said generator is operating UV light contacts the chlorine dioxide generating solution when present within the activation vessel to produce the activated solution containing chlorine dioxide;

a source of chlorine dioxide generating solution in communication with the activation vessel;

a media pad constructed and arranged to allow air to pass through and being in communication with the activation vessel such that the activated solution from the activation vessel flow through the media pad to intimately contact air flowing through the media pad during operation of the air cleanser to provide cleansed air and at least a portion of solution leaving the media pad is returned to the activation vessel;

at least one air inlet and at least one air outlet in communication with the media pad to supply air to the media pad and allow cleansed air leaving the media pad to exit the air cleanser during operation of the air cleanser; and air moving structure constructed and arranged to provide an air flow through the media pad during operation of the air cleanser.

The objectives of the invention are further met by a method of cleansing air using an air cleanser comprising:

exposing a chorine dioxide generating solution to UV light in an activation vessel to form an activated solution containing chlorine dioxide;

transferring the activated solution to a media pad;

passing air through the media pad such that the activated solution from the activation vessel flows through the media pad and intimately contacts the air flowing through the media pad;

returning at least a portion of solution leaving the media pad to the activation vessel; and adding chlorine dioxide generating solution to the activation vessel.

The objectives of the invention are further met by an air cleanser comprising:

an activation vessel constructed and arranged to contain a chlorine dioxide generating solution that forms an activated solution containing chlorine dioxide upon exposure to UV light;

a source of UV light constructed and arranged to provide UV light to said activation vessel such that when said generator is operating UV light contacts the chlorine dioxide generating solution when present within the activation vessel to produce the activated solution containing chlorine dioxide;

a source of chlorine dioxide generating solution in communication with the activation vessel;

water curtain structure constructed and arranged to allow air to pass through and being in communication with the activation vessel such that the activated solution from the activation vessel is brought into intimate contact with the air flowing through the water curtain structure during operation of the air cleanser to provide cleansed air and at least a portion of solution leaving the water curtain structure is returned to the activation vessel;

at least one air inlet and at least one air outlet in communication with the water curtain structure to supply air to the water curtain structure and allow cleansed air leaving the water curtain structure to exit the air cleanser during operation of the air cleanser; and air moving structure constructed and arranged to provide an air flow through the water curtain structure during operation of the air cleanser.

The objectives of the invention are also met by a method of cleansing air using an air cleanser comprising:

exposing a chorine dioxide generating solution to UV light in an activation vessel to form an activated solution containing chlorine dioxide;

transferring the activated solution to water curtain structure;

passing air through the water curtain structure such that the activated solution from the activation vessel flows through the water curtain structure and intimately contacts the air flowing through the water curtain structure to produce cleansed air;

returning at least a portion of solution leaving the water curtain structure to the activation vessel; and adding chlorine dioxide generating solution to the activation vessel.

BRIEF DESCRIPTION OF THE DRAWINGS

FIG. 1 illustrates a side view of a chlorine dioxide generator according to the present invention;

FIG. 2 illustrates a side view of UV bulbs and a reaction vessel according to the present invention;

FIG. 3 illustrates a 3 is a top view of UV bulbs in relation to ultrasonic plates according to the present invention;

FIG. 4 illustrates a side view of a reaction vessel, UV bulbs and ultrasonic discs according to the present invention;

FIG. 5 illustrates a view of a reaction vessel having three liquid line attachments;

FIG. 6 illustrates a view of an air stream embodiment according to the present invention.

FIG. 7 illustrates a combined UV reaction vessel according to the present invention;

FIG. 8 illustrates an embodiment of a UV reaction vessel and air cleanser;

FIG. 9 illustrates an embodiment of a UV reaction vessel for providing a liquid chlorine dioxide stream;

FIG. 10 illustrates an air cleanser according to the present invention;

FIG. 11 illustrates an air cleanser according to the present invention;

FIG. 12 illustrates an air cleanser according to the present invention;

DETAILED DESCRIPTION OF PREFERRED EMBODIMENTS

Figure 1:
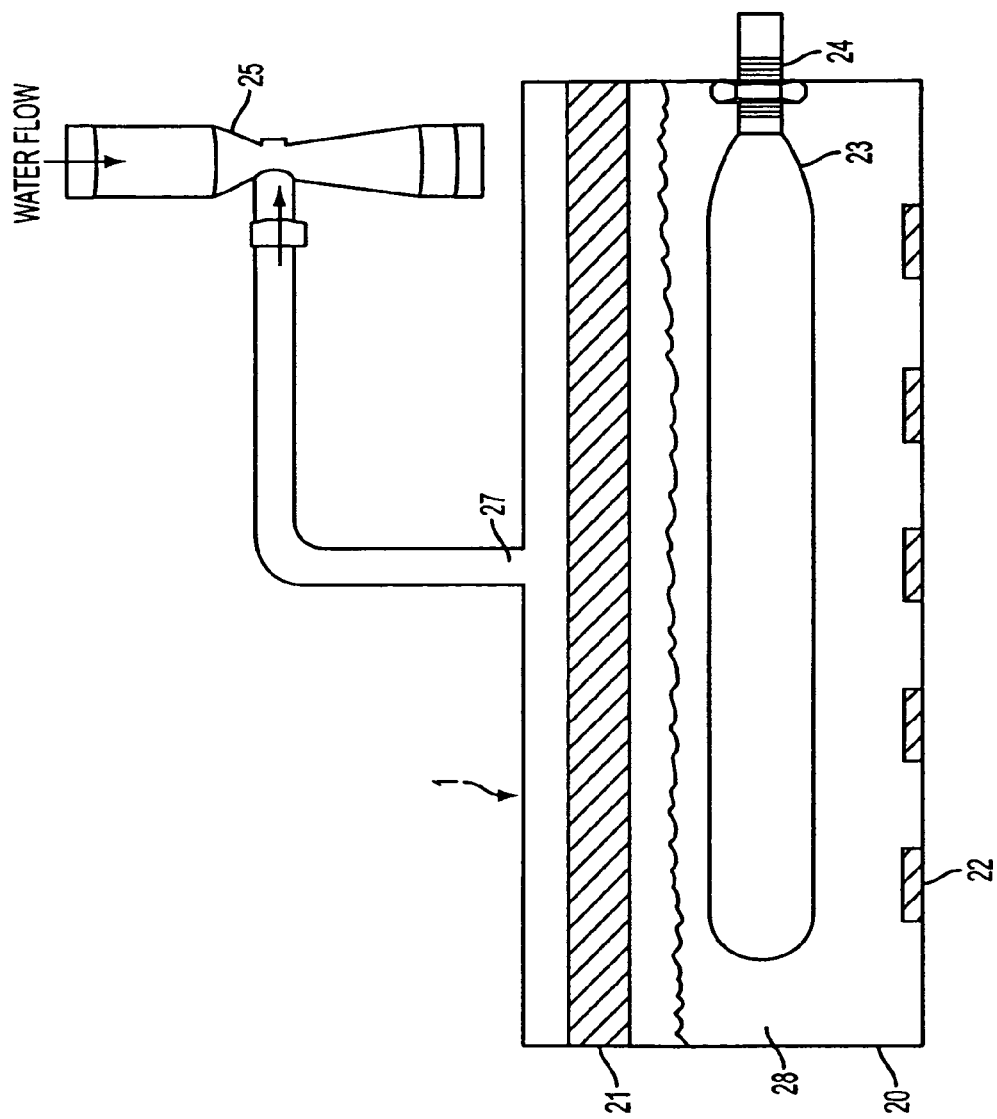

The present invention relates to a novel chlorine dioxide generator. The present invention also relates to a novel method to produce and simultaneously recover chlorine dioxide on demand by exposing a chlorine dioxide generating solution to UV light in a chlorine dioxide generator.

The chlorine dioxide generating solution comprises at least one active agents that forms chlorine dioxide upon exposure to UV light, which is dissolved or dispersed in an aqueous medium. Examples of chlorine dioxide generating solutions include, but are not limited to active agents comprising chlorites, such as alkali metal chlorites or alkaline earth chlorites, chlorine, hypochlorites, trichloro isocyanuric acid, and/or salts of organic chlorine donors, such as sodium dichloroisocyanuate (NaDDC), which are dissolved or dispersed in an aqueous medium. The aqueous medium can comprise water, tap water, reprocessed water, recycled water, water containing desired additives, and recycled spent activated solution. Preferably, the chlorine dioxide generating solution comprises sodium chlorite as the active agent. Technical grade sodium chlorite can be utilized if desired. When sodium chlorite is utilized, preferably it is present in an amount of from about 1 to about 5% by weight.

While not preferred, a solid form of the chlorine dioxide generating solution can be used in a manner similar to how chlorine tablets used in pools, which dissolve slowly releasing chlorine. This type of mechanism can be used to supply fresh chlorine dioxide generating solution as is dissolves slowly from a tablet. Examples include solid tablet feeders, solid-concentrate cartridge dissolving feeders, flowable powder feeders, and the like. Solid tablet feeders are well known to those skilled in the art. They have been employed in water and wastewater treatment, swimming pools and hot tubs.

Once the chlorine dioxide generating solution is exposed to UV light, it forms an activated solution containing chlorine dioxide and also usually contains chloride ions, chlorate ions, and other oxychloro species dissolved or dispersed in the aqueous medium.

The chlorine dioxide generating solution and activated solution are contained in a reaction vessel, also referred to as an activation vessel. The reaction vessel can be formed from any suitable material that is resistant to the chlorine dioxide generating solution, activated solution, chlorine dioxide and any other additives utilized. Examples of reaction vessel materials include glass, quartz, plastic, and/or metals.

The reaction vessel can be any shape or size as desired. Preferably, the reaction vessel is shaped so that readily available cylindrical UV bulbs can easily be mounted within the reaction vessel.

The reaction vessel contains at least one chlorine dioxide exit through which generated chlorine dioxide can be continuously evacuated from the reaction vessel during operation of the chlorine dioxide generator. The reaction vessel also preferably contains at least one solution inlet and at least one solution outlet through which the level and/or replenishment of chlorine dioxide generating solution can be adjusted in the reaction vessel by adding new chlorine dioxide generating solution through the solution inlet and by removing spent activated solution having chlorine dioxide removed there from through the solution outlet. Since the fresh chlorine dioxide generation solution and activated solution are intermixed, some chlorine dioxide generating solution may also be discarded through the solution outlet as well. The flow of fresh chlorine dioxide generation solution into the solution inlet can be controlled by a metering pump, a solenoid operated valve with a timer to meter a carefully controlled rate of chlorine dioxide generating solution, or other controls. Alternatively, the aqueous medium and the active agent that forms chlorine dioxide upon exposure to UV light can be added to the reaction vessel separately through separate solution inlets with the flow of each being independently controlled so that the chlorine dioxide generation solution is formed within the reaction vessel. The flow of spent activated solution through the solution outlet can be controlled using a solenoid valve and float switch, or other controls as desired. The reaction vessel can also contain an overflow line to prevent overfilling of the reaction vessel with chlorine dioxide generating solution and/or aqueous medium.

UV light sources are now well known. Any suitable UV light source can be used in the present chlorine dioxide generator. For example, one or more UV bulbs can be used as the source of UV light. The UV bulbs preferably run along most of the width or length of the reaction vessel illuminating the entire contents with UV light when the generator is operating. The UV bulbs are preferably positioned inside the reaction vessel to maximize exposure of the chlorine dioxide generating solution. Cylindrical UV bulbs can be used. Low pressure mercury vapor bulbs are suitable. The amount of UV light is controlled by a UV controller. Preferably, the predominate UV light wavelength is less than 260 nm to reduce adsorption of UV light by the chlorine dioxide, and more preferably the UV light wavelength utilized is 254 nm. Suppliers of suitable UV bulbs include Cathodeon Ltd., Hellma USA, and Heralius Inc.

Sources of ultrasonic vibrations are now well known. Any suitable ultrasonic device can be utilized in the present invention to agitate the activated solution during production of chlorine dioxide. For example, a series of ultrasonic piezoelectric plates can be installed along the middle of the reaction vessel. Preferably, ultrasonic piezoelectric plates are mounted inside of the reaction vessel to directly contact the activated solution. Without being bound by any theory, it is believed that the ultrasonic discs translate electrical power into high frequency ultrasonic vibrations that produce an ultrasonic wave in the activated solution. The ultrasonic wave rapidly drives dissolved or dispersed chlorine dioxide from the activated solution, which can be in the form of bubbles. Preferably, the piezoelectric plates vibrate at ultrasonic frequency from 1.6 MHz to 2.5 MHz. Other ultrasonic devices operating at lower frequencies, such as in the kHz range, or even higher frequencies, can also be used to drive the chlorine dioxide gas from the solution, as desired for the particular application. Suppliers of suitable ultrasonic piezoelectric plates include American Piezo Ceramics, Blue Wave Ultrasonics, Piezo Technologies, Piezo Solutions, Omegasonics, and Ultrasonic Power Corp (UPC).

Before the chlorine dioxide is evacuated from the reaction vessel through the chlorine dioxide exit, it passes through a gas permeable structure inside of the reaction vessel. If desired, the gas permeable structure can be located after the chlorine dioxide exit, although that arrangement is not preferred. Gas permeable structures are now well known. A gas permeable structure should be selected which is capable of containing the chlorine dioxide generating solution and activated solution within the reaction vessel but which allows the chlorine dioxide gas to pass therethrough. Suitable gas permeable structures are commercially available.

Evacuation of the produced chlorine dioxide from the reaction vessel is facilitated by using evacuation structure. Examples of evacuation structure include an air stream and reduced pressure. Evacuation of chlorine dioxide from the reaction vessel should be simultaneous with the production of chlorine dioxide to minimize exposure of chlorine dioxide to UV light and to provide on demand chlorine dioxide.

In one embodiment, the gas permeable structure and chlorine dioxide exit are connected to a water-driven venturi eductor that reduces the pressure in the reaction vessel thereby facilitating the flow of free chlorine dioxide from the activated solution and through the structure into an aqueous flow line. Chlorine dioxide is highly soluble in water and immediately forms an aqueous chlorine dioxide solution in the aqueous flow line. The chlorine dioxide solution can then be piped to its point of use. The type of water used can be as desired for the particular application. For example, tap water, process water, recirculating wash water, and recycled water can be used as desired. If tap water is utilized, a water tap connector can be mounted on the eductor so that it can be easily connected to tap water. For example, the eductor can be run to provide concentrations chlorine dioxide dissolved in the water, such as about 1 to about 3000 parts per million (mg/liter), as desired for the particular application.

If gaseous chlorine dioxide is preferred, instead of using the water-driven venturi eductor a small fan can be used to drive off the chlorine dioxide produced in the reaction vessel and form an air stream containing the chlorine dioxide. The fan can be mounted so that it blows air into the reaction vessel and across the surface of the activated solution or so that it creates a reduced air pressure in the reaction vessel such that air flows into the reaction vessel and across the surface of the activated solution. Small amounts of water vapor droplets may also be expelled through the exit tubes that project outwards from the reaction vessel. If desired, when using an air stream the gas permeable structure can be excluded. The air stream mixed with chlorine dioxide produces a dilute mixture of air, chlorine dioxide, and water vapor that can be piped to its point of use. The concentration of chlorine dioxide can be accurately controlled, for example, by controlling the fan speed and/or the amount of chlorine dioxide generating solution added to the reaction vessel. The concentration of chlorine dioxide in the air stream leaving the generator is usually about 5 to about 100 ppm, but can be selected as desired for the particular application.

The concentration and amount of chlorine dioxide can be continuously adjusted by adjusting the flow of the chlorine dioxide generating solution, the intensity of the UV light, the fan speed if present, and amount of vacuum supplied by the eductor if present. Preferably, the concentration and amount of chlorine dioxide is adjusted by adjusting the flow of chlorine dioxide generating solution into the reactor. If desired, chlorine dioxide sensors can be utilized in combination with a computer and/or feedback from an apparatus using the chlorine dioxide to control the production of chlorine dioxide. Other sensors, such as pollutant sensors like hydrogen sulphide, can also be utilized in the control of the chlorine dioxide.

Preferably, the controls, source of UV light, source of ultrasonic vibrations, fan, metering pump and any other electrical devices utilized operate on 110V or 220V.

The invention will now be described with reference to the attached Figures. FIG. 1 is a schematic drawing showing chlorine dioxide generator. The reaction vessel (20) houses two or more cylindrical UV bulbs (23). The UV bulbs are connected to the reaction vessel (20) by means of a threaded mount (24). A series of ultrasonic piezoelectric plates (22) are installed in the bottom of the reaction vessel (20) in a manner so that the piezoelectric plates come into direct contact with the activated solution inside the reaction vessel (20) during operation. A gas permeable structure (21) retains the activated solution within the reaction vessel (20) but allows gaseous chlorine dioxide to pass through and out the chlorine dioxide exit (27).

Figure 2:
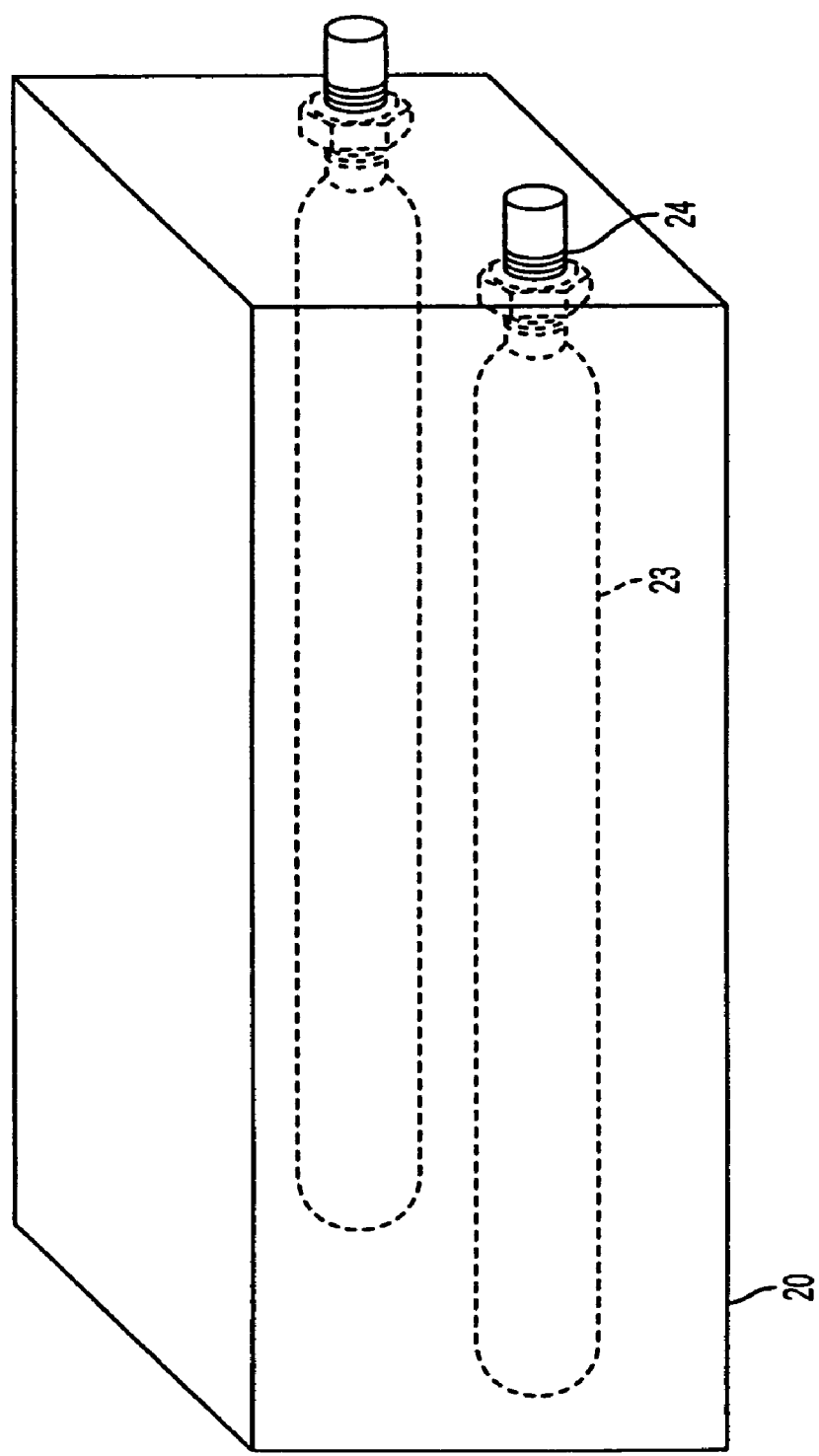
Figure 3:
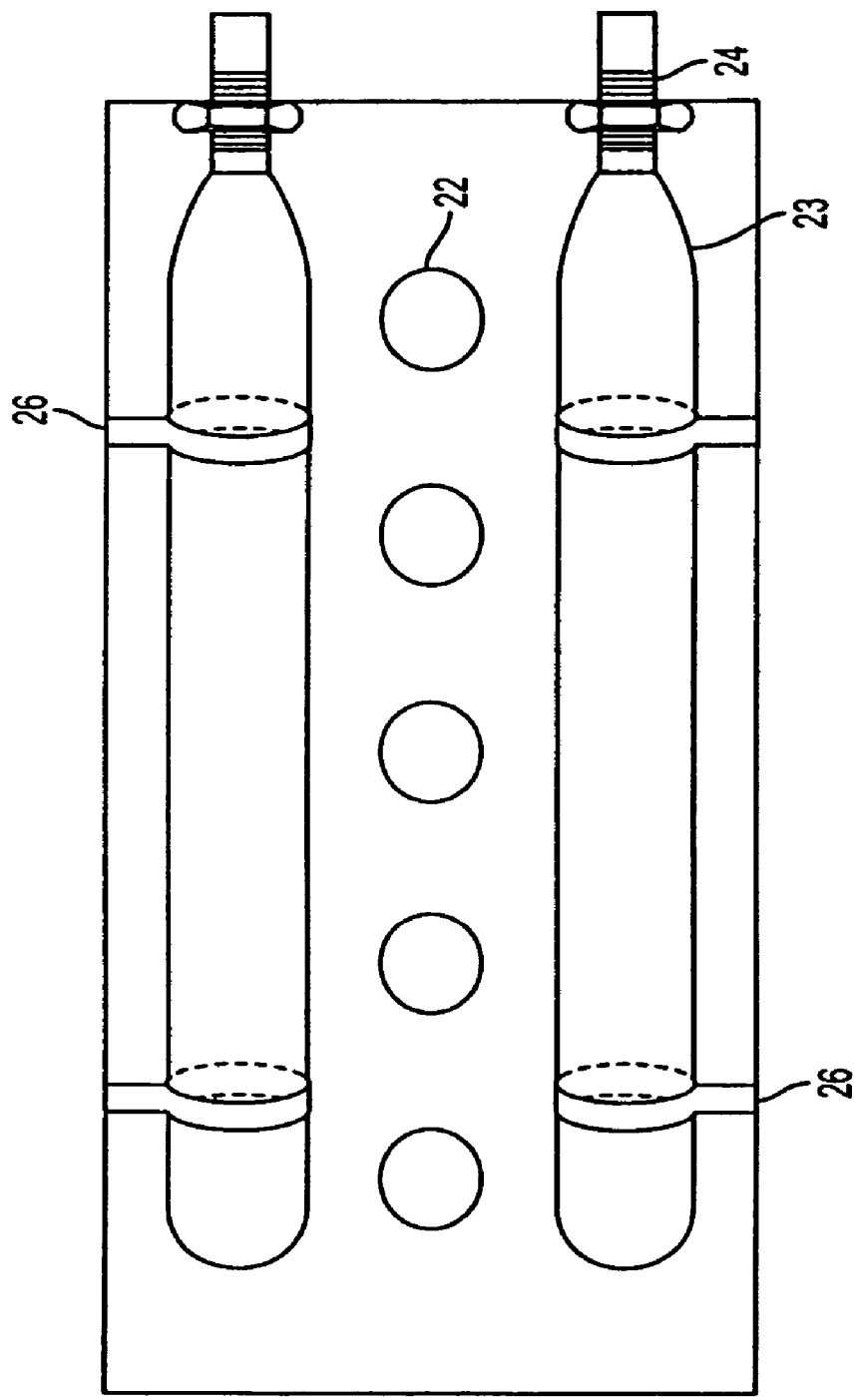
Figure 4:
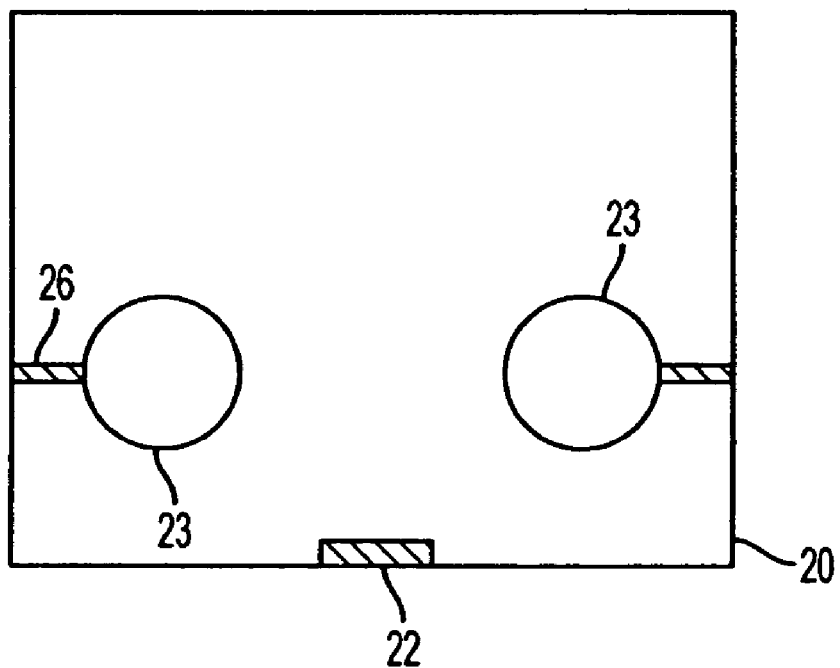

FIG. 2 is a perspective drawing showing the placement of the UV bulbs (23) within the reaction vessel (20). FIG. 3 is a top view illustrating the arrangement of the UV bulbs (23) in relation to the ultrasonic piezoelectric plates (22). The UV bulbs are fastened to the reaction vessel by a threaded mount (24) and by bulbs (26). The threaded mount (24) allows the easy removal and replacement of the UV bulbs. FIG. 4 shows a side view of the reaction vessel (20) and orientation of UV bulbs (23) and ultrasonic discs (22).

Figure 5:
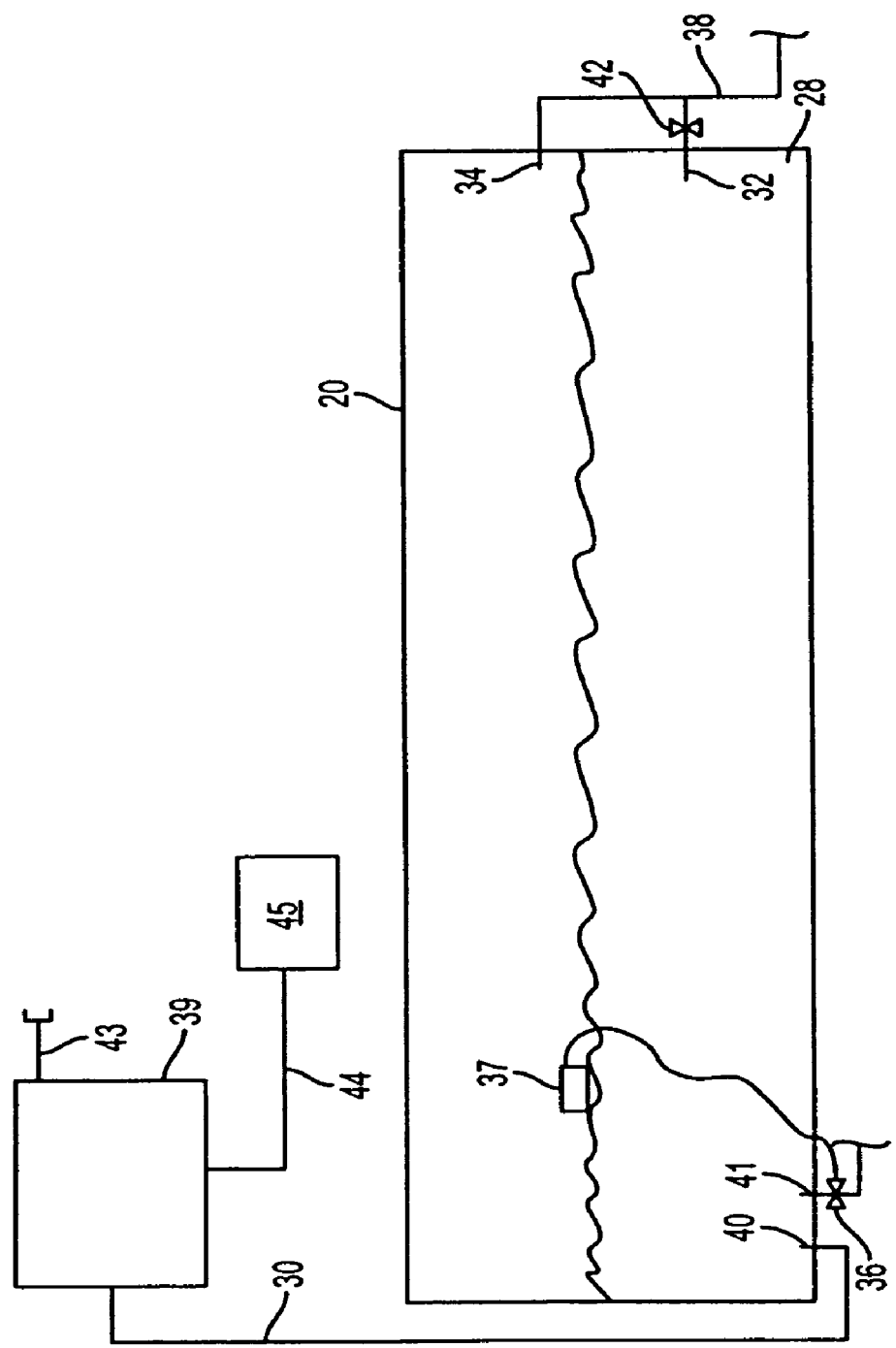

FIG. 5 shows the outside of the reaction vessel with three liquid line attachments. An active agent line (30) supplies the sodium chlorite or other active agent to the reaction vessel (20) through an active agent inlet (40). The active agent can be pumped into the reaction vessel (20) using a standard metering pump (39). The metering pump is preferably operated using 110V or 220V (43). The active agent is stored in a container (45) and is supplied to the metering pump (39) using supply line (44). The liquid level is maintained using a float switch (37) connected to a solenoid valve (36). When the liquid level drops, the float switch (37) activates the solenoid valve (36) which allows water to enter the reaction vessel (20) through water inlet (41) until a desired liquid level is reached and the float switch (37) shuts off the solenoid valve (36). The reaction vessel (20) is equipped with a solution outlet (32) to remove spent reactants and can be controlled with a solenoid valve (42). These devices keep the liquid level in the reaction vessel at a constant depth and volume. An overflow outlet (34) is also attached for additional safety and control. The overflow outlet (34) and solution outlet (32) merge to form a waste line (38), where spent reactants can be disposed as required by law. If a fan is utilized, as shown in FIG. 6, the water may have to be replenished more often due to increased evaporation and water droplet removal.

Figure 6:
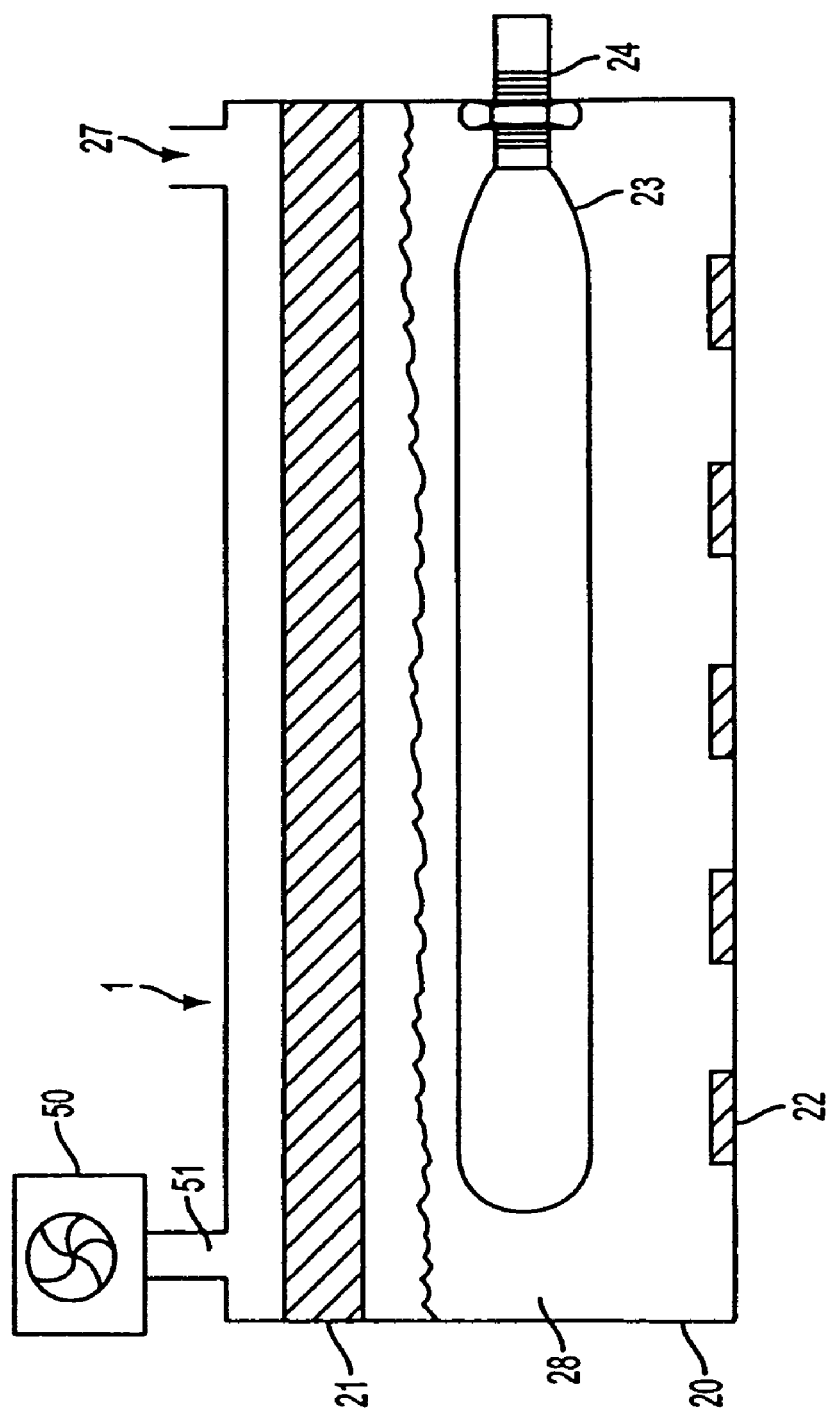

FIG. 6 illustrates an alternative embodiment in which the chlorine dioxide is maintained in the gaseous form, i.e. not dissolve it in an aqueous stream. A device for projecting a gaseous stream of chlorine dioxide is shown in attached pictures of reaction vessel (20). In this embodiment, a fan (50) blows air into the reaction vessel (20) through air inlet (51) which drives off the chlorine dioxide produced in the reaction vessel (20) and exits through the chlorine dioxide exit (27). While a gas permeable structure (21) is shown in FIG. 6, the generator (1) can be run without the use of the gas permeable structure (21). If no gas permeable structure (21) is utilized, small amounts of water vapor droplets may also be expelled through the chlorine dioxide exit (27).

In some cases, especially if a larger flow of chlorine dioxide generating solution is required, it is preferable to separate the photoactivation of the chlorine dioxide generation solution to form activated solution and recovery of chlorine dioxide from the activated solution into two steps. This means that the photocatalytic reaction of the chlorine dioxide generating solution in the reaction vessel should be complete before entering a separate separation chamber and being agitated by the piezoelectric plates. This would reduce the amount of chlorine dioxide generating solution present with the spent reactants being discarded, thereby increasing yield and efficiency. Thus, in this embodiment, the source of ultrasonic vibrations, chlorine dioxide exit, solution exit and evacuation structure as described herein above are located in the separation chamber, not the reaction vessel.

There are several configurations possible for the UV bulb and flow path of the chlorine dioxide generating solution. UV water sterilization systems utilize a helical or serpentine path of water around and proximate to a low power mercury bulb. It has now been found that such a configuration could be used to irradiate the chlorine dioxide generation solution according to the present invention to produce chlorine dioxide.

It has also now been found that UV microwave powered electrodeless bulbs, such as those disclosed in U.S. Pat. No. 5,614,151, the complete disclosure of which is incorporated herein by reference, offer several distinct advantages to conventional low pressure mercury vapor bulbs. The bulb operates using microwave radiation to energize a UV-emitting bulb. Since the bulb does not use electrodes, the bulb can operate as low, medium, or high pressure bulbs, and bulb life is extended almost indefinitely. This type of bulb has demonstrated low pressure mercury wavelengths at about 10 times the power of conventional systems. Further, since the constraints of electrodes do not apply, the bulbs can be made virtually in any shape.

Using the electrodeless bulb design, I have now combined the UV bulb, reaction vessel and flow path of the chlorine dioxide generating solution to be housed together in a single combined UV reaction vessel. This is a distinct advantage in that it increases the surface area and exposure of the chlorine dioxide generating solution to the UV source. It also simplifies the reaction vessel design and reduces its complexity and cost considerably.

Figure 7:
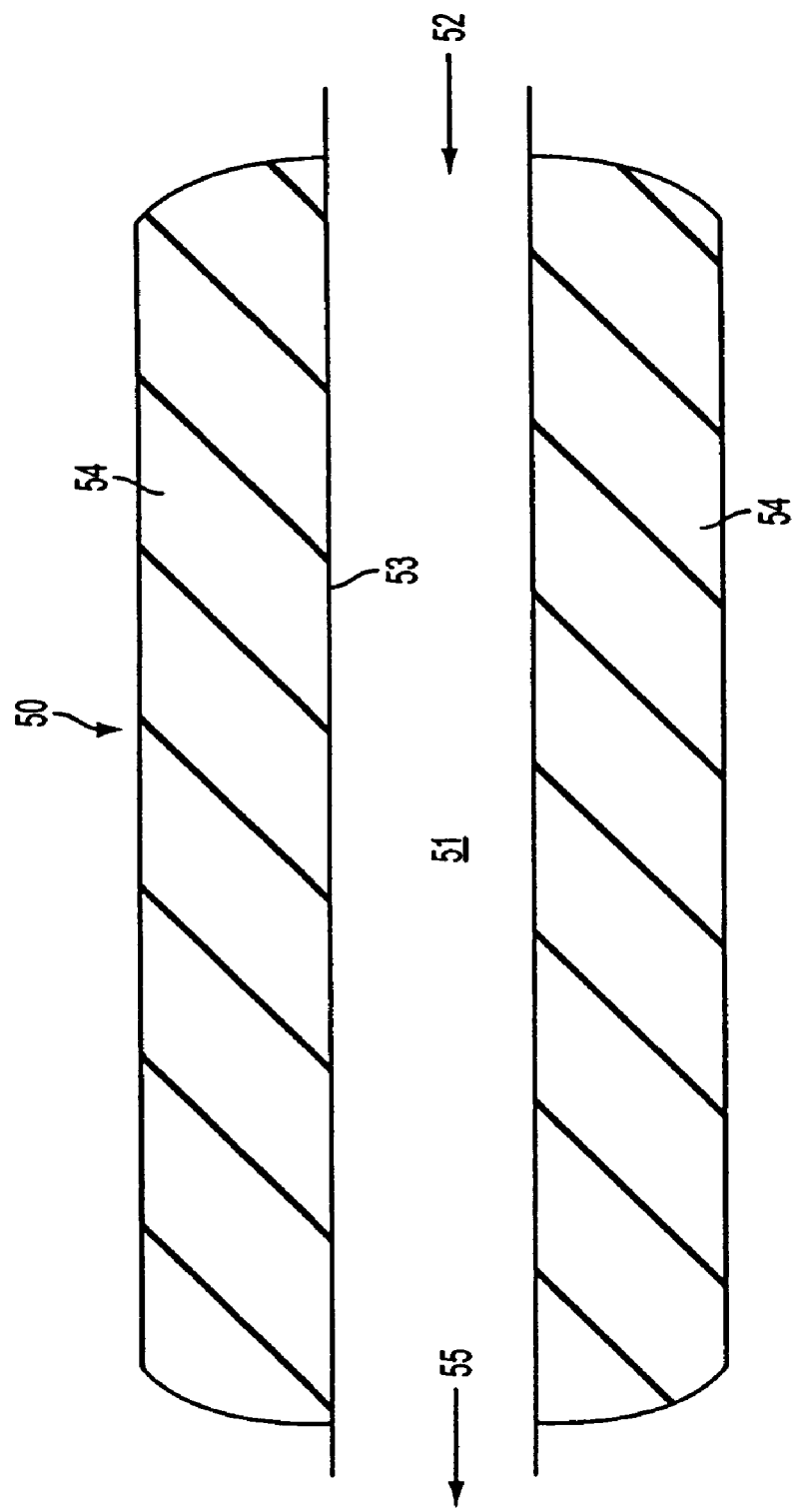

FIG. 7 shows a combined UV reaction vessel (50) in which the chlorine dioxide generating solution enters the inner annulus (51) of the UV reaction vessel (50) at (52) and is conducted along the UV emitting surface (53) of the UV bulb (54). The UV bulb (54) is preferably an electrodeless bulb design containing a mixture of argon and mercury vapor. While argon and mercury vapor are shown, other nobel gases can be used instead of or in addition to argon. The turbulence created by the flow of the chlorine dioxide generating solution ensures that fresh chlorine dioxide generating solution is always in contact with the UV emitting surface (53). Activated solution exiting the inner annulus (51) at (55) contains aqueous chlorine dioxide and also usually contains chloride ions, chlorate ions, and other oxychloro species. The activated solution can either be used immediately since it contains chlorine dioxide or conducted to a separation chamber and agitated using a source of ultrasonic vibrations and evacuation structure to drive the chlorine dioxide from the activated solution leaving the other reactants in an ionic solution. An air stream or aqueous stream of chlorine dioxide can be formed using the evacuation structure as described herein above with reference to other embodiments.

If the activated solution containing chlorine dioxide is used prior to separation of the chlorine dioxide, additional additives can be mixed with the chlorine dioxide generating solution prior to photoactivation. Examples of additives may be surfactants, water softening agents, dispersants, solvents, wetting agents. If sodium chlorite is used as the active agent, conventionally, these materials have to be added or mixed with acidified sodium chlorite solution. The low pH of such acidified chlorite solutions may preclude adding many types of additives. The ability to add these agents prior to the UV initiated reaction and formation of chlorine dioxide allows the production of agents useful in a variety of commercial applications such as hard surface cleaning, sanitizing equipment and surfaces, and oil and water well injection.

Figure 8:
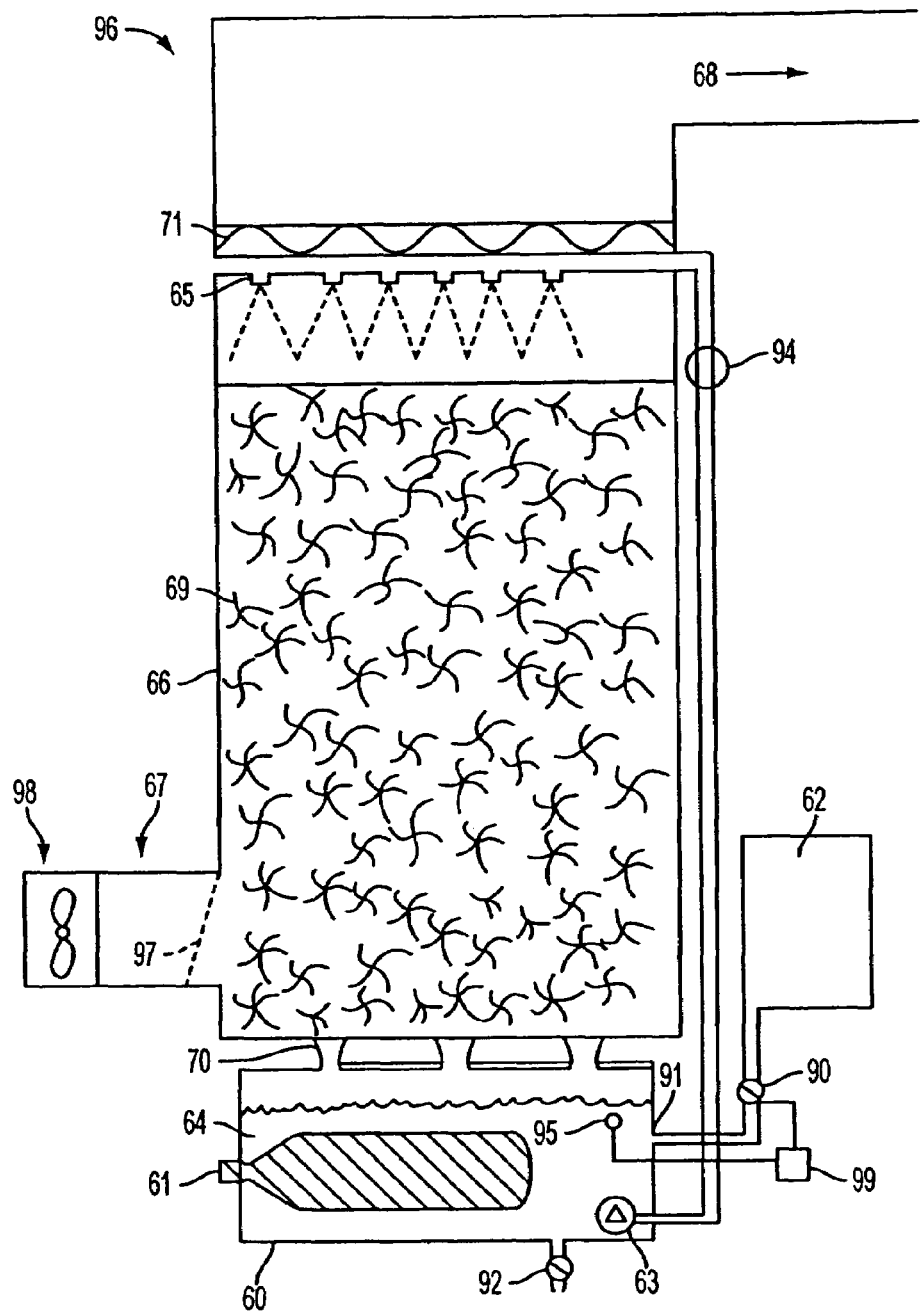

In certain cases it is useful to treat an air stream with chlorine dioxide. This is accomplished by circulating the chlorine dioxide generation solution through a packed column which provides for liquid/gas contact, as shown in FIG. 8. The chlorine dioxide produced in the UV activation vessel is then available to neutralize chemical or biological contaminants in the air stream.

Chemical contaminants include but are not limited to hydrogen sulfide and reduced organic sulfur compounds such as mercaptans and thiols. The alkaline pH of the chlorine dioxide generating solution also facilitates in the stability and removal of acid gases. Biological contaminants include but are not limited to bacteria, spores, viruses, molds, fungi, etc. Airborne particulate matter is also removed in the packed column.

An air cleansing apparatus (96) is shown in FIG. 8. In this apparatus (96) the activation vessel or reaction vessel (60) is similar to the main embodiment described above in that the UV bulbs (61) are mounted in a horizontal orientation. The vessel (60) can be of any shape or volume as desired for the particular application. An example of a suitable size is about 20 liters. A chlorine dioxide generating solution tank (62) is connected to a solution inlet (91). The amount of chlorine dioxide generating solution supplied from the tank (62) can be controlled by metering structure (90), such as a metering pump or solenoid-operated valve to vessel (60). The chlorine dioxide generating solution (64) upon exposure to the ultraviolet radiation from the UV bulbs (61) is photochemically oxidized to form an activated solution containing chlorine dioxide. The activated solution in this embodiment may be mixed with chlorine dioxide generating solution in this embodiment. The reaction primarily occurs at or near the surface of the bulbs (61). A preferred chlorine dioxide generating solution in this embodiment comprises aqueous sodium chlorite at a concentration of about 1 to about 20% by weight.

The produced chlorine dioxide present in the activated solution is quickly removed from the vessel (60) by a circulating submergible water pump (63). This avoids the decay of chlorine dioxide by UV and visible light produced by the bulbs (61). The wavelength of UV that decays chlorine dioxide is mostly greater than 300 nm. The vessel (60) is also equipped with a drain (92) to periodically remove spent chlorine dioxide generating solution (64). Preferably, the pump (63) and solution inlet (91) are on opposite sides of the vessel (60) to reduce the amount of fresh chlorine dioxide generating solution picked up by pump (63) and mixed with the activated solution.

The vessel (60) should be fitted with a cover to prevent evaporation of chlorine dioxide from the circulated chlorine dioxide generating solution. The circulating chlorine dioxide concentration in the activated solution can be maintained at any desired level, such as from about 1 to about 5 ppm, by metering the flow of chlorine dioxide generating solution to the vessel (60). Preferably, the chlorine dioxide can be measured using an optional photo-spectrometer (94) If high chemical loads are present in the airstream entering the apparatus (96) greater circulating concentrations of chlorine dioxide may be required.

A submergible water pump (63) is present in the vessel (60). The function of the water pump (63) is to circulate the mixture of activated solution to dispersing structure (65), such as spray nozzles, located at the top of the column (66).

The activated solution can be dispersed to the column (66) in any desired manner, such as by allowing the activated solution to pour over the packing material (69). However, the use of spray nozzles (65) is preferred. The column (66) can be situated above the vessel (60) to provide gravity feed of the activated solution from the column (66) to the reaction vessel (60).

The column (66) can be any shape or dimension as desired for the particular application. An example of a suitable size is a rectangular shape of about 2 feet wide by 2 feet deep by 3 feet high. The column (66) is fitted with at least two openings, air inlet (67) and air outlet (68). At least one air inlet (67) opening near the bottom of the column (66) allows the passage of an air stream to move in and upwards through the column (66) in counter current direction to the flow of the activated solution containing chlorine dioxide. At least one air outlet (68) opening near the top of the column (66) allows the air stream to flow out of the column (66). Preferably, the outlet (68) and inlet (67) are located on opposite sides of the column (66). By using a counter current flow, the transfer of chlorine dioxide from the activated solution to the air stream is maximized.

The column (66) is preferably filled with a high surface area packing material (69) to maximize contact between the air stream and the activated solution. An example of a suitable packing material is NuPac (55 square ft per cubic ft., manufactured by Lantec Products, Inc.). However, any suitable inert packing material can be used, such as beads, saddles, cubes, pads, or irregular shaped pieces of plastic, ceramic, metal, or glass. This counter current flow of the air stream and activated solution provides a sufficient concentration of chlorine dioxide to neutralize airborne contaminants. A plurality of liquid outlets (70), such as perforations perforated along the bottom of the column (66), allow the activated solution to drain back into the vessel (60). Most of the chlorine dioxide present in the activated solution will be transferred to the air stream in the column (66).

The spray nozzles (65) mounted at the top of the column (66) distribute the activated solution evenly throughout the column (66) and if packing material (69) is present to evenly distribute the activated solution over the upper surface of the packing material (69) to provide an even flow through the column (66). A mist eliminator pad (71) is disposed above the spray nozzles to remove particulate amounts of activated solution from the air stream. A screen (97) can be used to retain the packing material (69) in the column (66). The air stream can be provided by a blower, fan, or any air-moving device (98) as desired. The air-moving device should supply an adequate pressure to force the air through the packed column.

The utilization of dissolved chlorine dioxide produced in this embodiment is unique and non-obvious. Chlorine dioxide exists as a true gas in the activated solution and is therefore available for the neutralization reactions mentioned above. The activated solution also can contain unreacted chlorite ions and photochemical reaction products such as chloride ions and various oxy-chloro species.

In the current embodiment, it is not necessary to separate the produced chlorine dioxide from the activated solution containing reactants prior to treatment of the air stream. The prior art using ultraviolet radiation teaches methods of separating and removing produced chlorine dioxide from the reaction products. There is no mention in the prior art with regard to directly employing the activated solution in the desired application.

The air stream need only contact chlorine dioxide in the column to effect decontamination or disinfection. In addition, only a small concentration, such as from about 1 to about 5 ppm, of chlorine dioxide is required in the circulating activated solution. The low circulating concentration of chlorine dioxide substantially improves upon the safety margin of prior art chemical oxidation gas scrubbing methods.

It is conceivable in this example to implement feedback regulation using an optional aqueous chlorine dioxide sensor (95). As the chlorine dioxide is consumed in the packed column, a drop in the chemical potential of the chlorine dioxide generating solution in the vessel (60) could be easily measured and relayed to a controller (99) for the chlorine dioxide generating solution metering structure (90). This structure is useful in optimizing the chlorine dioxide generating solution in circumstances requiring high decontamination loads such as in gas scrubbers. This aspect of the invention is distinct and stands in contrast to standard chemical feedback systems, which directly measure the gaseous pollutant concentration. Analytical methods for measurement of gases are more complex and expensive compared with aqueous methods.

This embodiment shown in FIG. 8 describes in a general way a method of generating chlorine dioxide in a circulating aqueous stream of water that is flowed counter current through an air/liquid contactor (column 66). This basic design concept can be incorporated into any system utilizing an air moving device and an air/liquid contactor. Practical examples of such systems include gas scrubbing devices, air washers, evaporative coolers, and humidifiers. While the prior art teaches many different types of scrubbing devices, air washers, evaporative coolers, and humidifiers, the prior art does not teach incorporating chlorine dioxide into any of these systems in the manner of the present invention.

Figure 9:
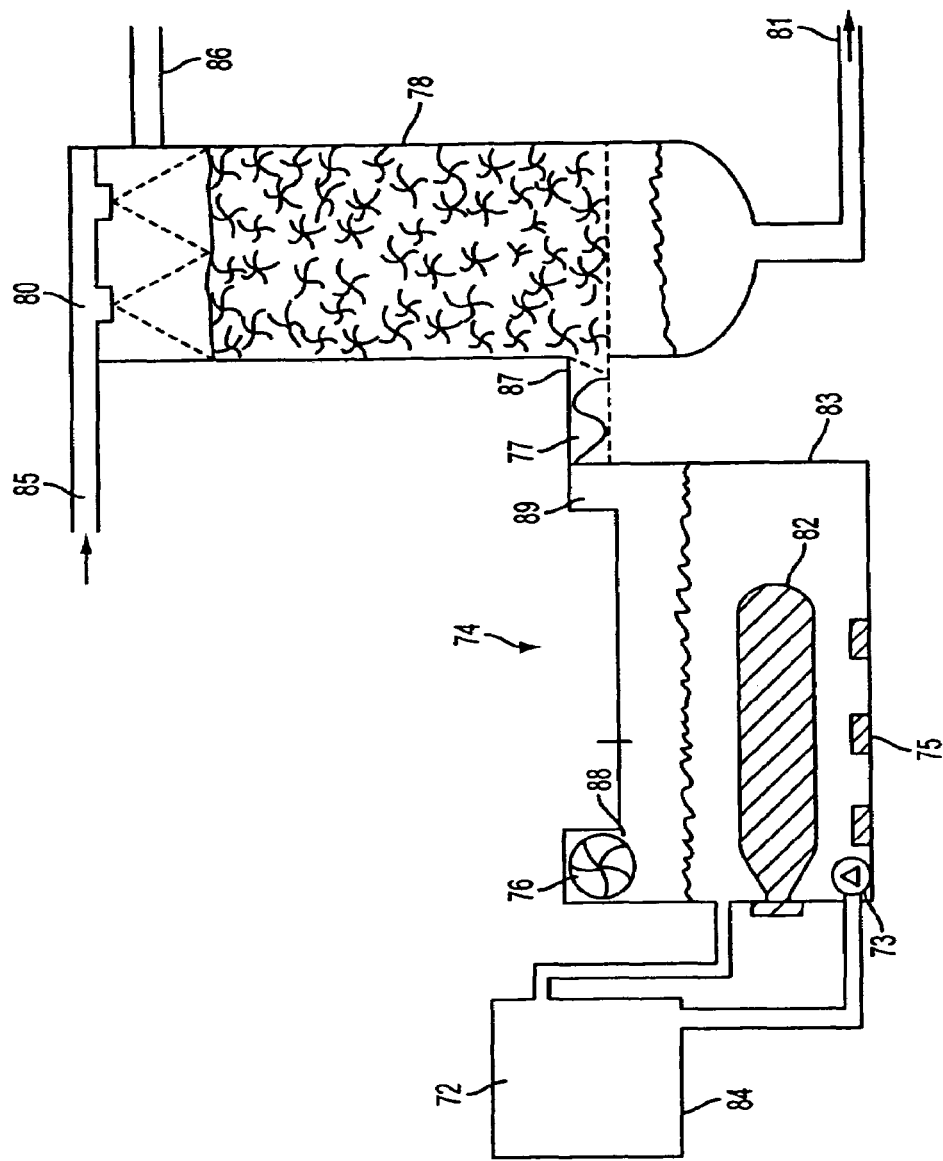

FIG. 9 illustrates an apparatus (74) in which chlorine dioxide gas produced in the current invention can also be dissolved into a stream of water. The aqueous chlorine dioxide solution can then conveyed to any point of use. Alternatively a re-circulating stream of water, such as process water from a poultry chill tank, may be treated by chlorine dioxide in the same manner.

The activation vessel or reaction vessel (83) is equipped with UV bulbs (82) as in the main embodiment. The chlorine dioxide generating solution (72) present in tank (84) is circulated through the vessel (83) and back to tank (84) by means of a submergible water pump (73). The photochemical reaction occurs at the surface of the bulbs (82). A preferred chlorine dioxide generating solution in this embodiment comprises about 5% by weight of sodium chlorite in water.

In this embodiment the limiting variable in the photochemical reaction is the surface area of the UV bulbs, not the concentration of chlorine dioxide generating solution, such as sodium chlorite, as in the main embodiment. The volume of the chlorine dioxide generating solution (72) in tank (84) is preferably large compared with the volume of chlorine dioxide generating solution in vessel (83). The tank holding the chlorine dioxide generating solution is usually about 20 to about 1000 liters, where as the activation vessel is generally about 1 to about 5 liters. The photochemical reaction will proceed as long is there is sufficient chlorine dioxide generating solution. As described above, when the chlorine dioxide generating solution is exposed to UV light, it forms activated solution containing reaction products and chlorine dioxide. As the apparatus is run, the amount of activated solution mixed with chlorine dioxide generating solution in the tank (72) will increase. This is similar to the prior art of Simpson (U.S. Pat. No. 6,171,558) who found that the production of chlorine dioxide was not dependant upon chlorite ion concentration and was constant over an extended time period.

However, the production of chlorine dioxide will decline gradually as the concentration of chlorite decreases below about 100 ppm.

The chlorine dioxide produced in vessel (83) can be quickly separated from the activated solution by the ultrasonic discs (75) located along the bottom of the vessel (83). The activated solution is vibrated at ultrasonic frequencies, such as 1.5 MHz, to release the produced chlorine dioxide gas.

An air-moving device (76) provides an air stream to the vessel (83) through air inlet (88) and air outlet (89) to propel the chlorine dioxide gas from vessel (83) through a mist eliminator pad (77) and air inlet (87) into a packed column (78). The mist eliminator pad (77) removes small particles of liquid, which are vaporized by the ultrasonic discs (75). The trapped liquid then flows back into the activation vessel (83).

The packed column (78) acts as a liquid/gas contactor, where the chlorine dioxide gas is dissolved into a liquid solvent, such as water. Chlorine dioxide gas is highly soluble in water and will be removed from the air stream flowing through the packed column (78). The column (78) is preferably filled with the high surface area packing material (79) to maximize contact between the liquid solvent and the chlorine dioxide gas. A liquid inlet (85) supplies liquid solvent to dispersing structure (80), such as spray nozzles, mounted at the top of the column (78) to provide even flow of the liquid solvent through the column (78). Any dispersing structure (80) can be used to disperse the solvent in the column (78), however, the use of spray nozzles (80) is preferred. The dissolved chlorine dioxide then exits the packed column (78) through the liquid outlet (81). The air stream exits the packed column (78) at air exit (86).

Figure 10:
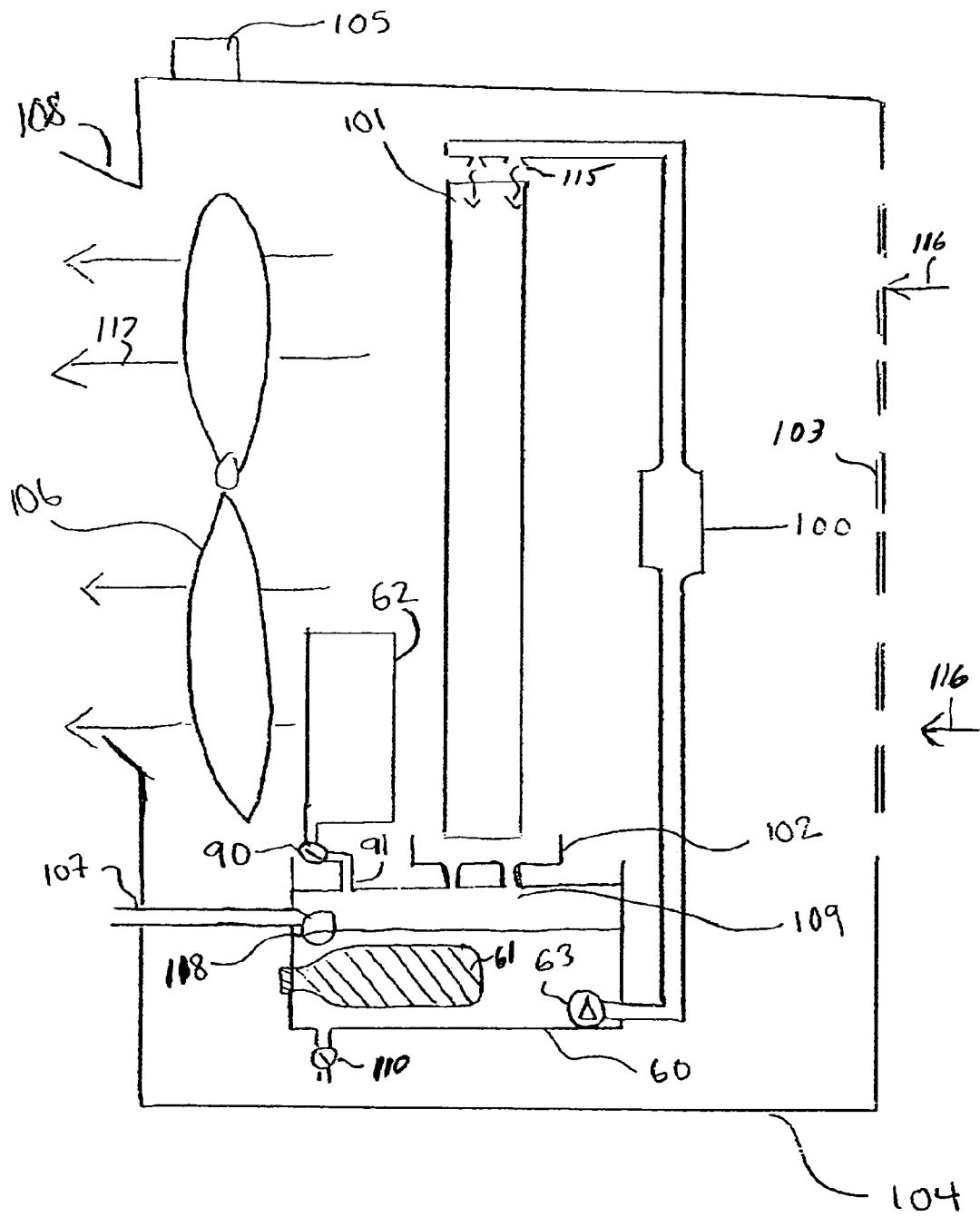

FIG. 10 shows an air cleaning device (104) similar to the one shown in FIG. 8. The present example is similar to a conventional industrial evaporative cooler but is equipped with the presently described novel chlorine dioxide generating apparatus. Instead of the air flow being directed vertically upwards through a packed column as shown in FIG. 8, the air flows horizontally through a high surface area media pad (101) using an air moving device (106). The media pad (101) should provide a large surface area for intimate mixing of air with activated solution containing chlorine dioxide, but should not restrict the passage of air with a large pressure drop. Examples of suitable materials include, but are not restricted to, an evaporative cooling pad, porous open-celled foam, or other high surface area material. Examples of commercially available materials include evaporative cooling pads from Munter Corporation and open-celled foams from Foamex Corporation. Ceramic foams have recently been made available for evaporative and humidification applications but are more expensive. For higher air flows, such as greater than 10,000 cfm, a water curtain can be used in place of the media pad (101).

The air (116) enters the device (104) through a pre-filter (103) before flowing through the media pad (101) and passes laterally through the device (104). An air guide (108) is installed on the front of the device (104) to facilitate mixing of room air with the cleansed air exiting the device (104) and to act as a safety cover for the air moving device (106). The air moving device (106) in this example is a fan. Other examples of suitable air moving devices (106) include blowers and air pumps.

The activation vessel (60) is similar to that shown FIG. 8 and fitted with UV bulb(s) (61). A chlorine dioxide generating solution tank (62) is connected to a solution inlet (91) of the activation vessel (60) to provide fresh chlorine dioxide generating solution to the activation vessel (60) as needed. The amount of fresh chlorine dioxide generating solution added to the activation vessel (60) can be metered using metering structure (90), such as solenoid operated valve or positive pressure pump.

After the chlorine dioxide generating solution is activated by UV light emanating from the UV bulb (61), activated solution containing chlorine dioxide exits the activation vessel (60) using a submersible pump (63). Alternatively, the activation vessel (60) can be located above the media pad (101) to allow gravity feed from the activation vessel (60). The submersible pump (63) circulates the activated solution through a sedimentation water filter (100) to remove any particulate contaminants such as dust, dead bacterial cell bodies, fine particulates, or inorganic particles. The filter (100) does not interfere with soluble salts or dissolved chlorine dioxide. Preferably, the filter (100) is removable for replacement when clogged. While the filter (100) is shown where the circulating solution leaves the reaction chamber, the filter (100) can be located at any desired stage in the process. Filter materials are now well known and any filter material that is compatible with chlorine dioxide, the chlorine dioxide generating solution selected, and reactants can be utilized. Examples of suitable filter materials include plastics, cellulose based materials, glass, metals and ceramics. The filter preferably is sized to remove particles less than about one micron.

After the activated solution containing chlorine dioxide is filtered by filter (100) it is dispersed over the media pad (101) using dispersion structure (115) located near the top of the media pad (101). The activated solution containing chlorine dioxide is allowed to percolate down through the media pad (101) where it intimately contacts the horizontally moving air stream in the open-celled pore structure of media pad (101). A significant portion of the chlorine dioxide is transferred from solution to the air stream in the media pad (101). The spent solution leaving the media pad (101) usually contains, reduced amounts of chlorine dioxide, reactants, chlorine dioxide generating solution that was not activated, as well as any airborne contaminates, such as dust, dead bacterial cell bodies, or particulates, caught by the media pad (101) and solution. The spent solution is captured by a drain pan (102) situated at the bottom of the media pad (101). The spent solution flows back into the activation vessel (60) though an inlet (109). Solution can be discarded from the activation vessel (60) using outlet and valve (110) as desired, such as when the concentration of reactants and contaminates reach undesired levels.

The entire solution should be replaced on a regular basis, such as every two or three months. This can be part a maintenance schedule and coincide with changing the sodium chlorite cartridge or adding new chlorine dioxide generating solution.

The flow rate of fresh chlorine dioxide generating solution to the activation vessel (60) is adjusted to provide a concentration of chlorine dioxide in the activated solution of preferably from about 1 to about 5 mg/L (ppm). In the current device (104), a flow rate of about 0.1 to about 0.25 ml/min of the fresh chlorine dioxide generating solution generated a $ClO_2$ concentration of about 1 to about 3 ppm in the activated solution supplied to the media pad (101).

Airborne contaminants such as bacteria, virus, fungi, allergen proteins, pollen, dust, inorganic particles, etc. are captured in the solution percolating through the open-celled foam matrix of the media pad (101) and destroyed or chemically detoxified by the chlorine dioxide, thus producing cleansed air (117) leaving the device (104). These contaminates are trapped and eventually removed by the water filter (100).

During operation of the air cleaner, a portion of the water percolating through the media pad (101) will evaporate and be diffused as water vapor into the cleansed air flow (117) generated by the air moving device (106). Water can be replaced by a connection to a water line (107) and regulated by a float valve (118). The fluid level is preferably maintained at a constant level throughout operation of the device (104).

The device (104) may also be equipped with a relative humidity sensor (105). This is useful for maintaining a comfortable relative humidity level in the air flow (117) that is well known to be between about 40% to about 60%. Thus, the device (104) has multifunction capabilities in controlling indoor climates. It can act as an evaporative cooler, humidifier, air cleaner, air washer, and vapor scrubber.

The present invention also overcomes the primary drawbacks of using evaporative coolers since the proliferation of mold, fungi, viruses, and bacteria is prevented by the presence of chlorine dioxide. In conventional evaporative coolers, bacteria and fungi growing on the various surfaces of evaporative pads results in a musty odor produced and it is this musty odor that has caused these device to be referred to as "swamp" coolers. In addition, the life of the evaporative media pad (101) is greatly extended since its regular replacement is not necessary.

Further, asthma and allergy sufferers and those with hay fever generally experience an increase in bronchial congestion when bacterial growth in evaporative coolers is not carefully maintained. The current device would also be useful for preventing the spread of virulent organisms such as *Legionella pneumophila* that have been responsible for many deaths attributed to its presence in building HVAC systems.

Figure 11:
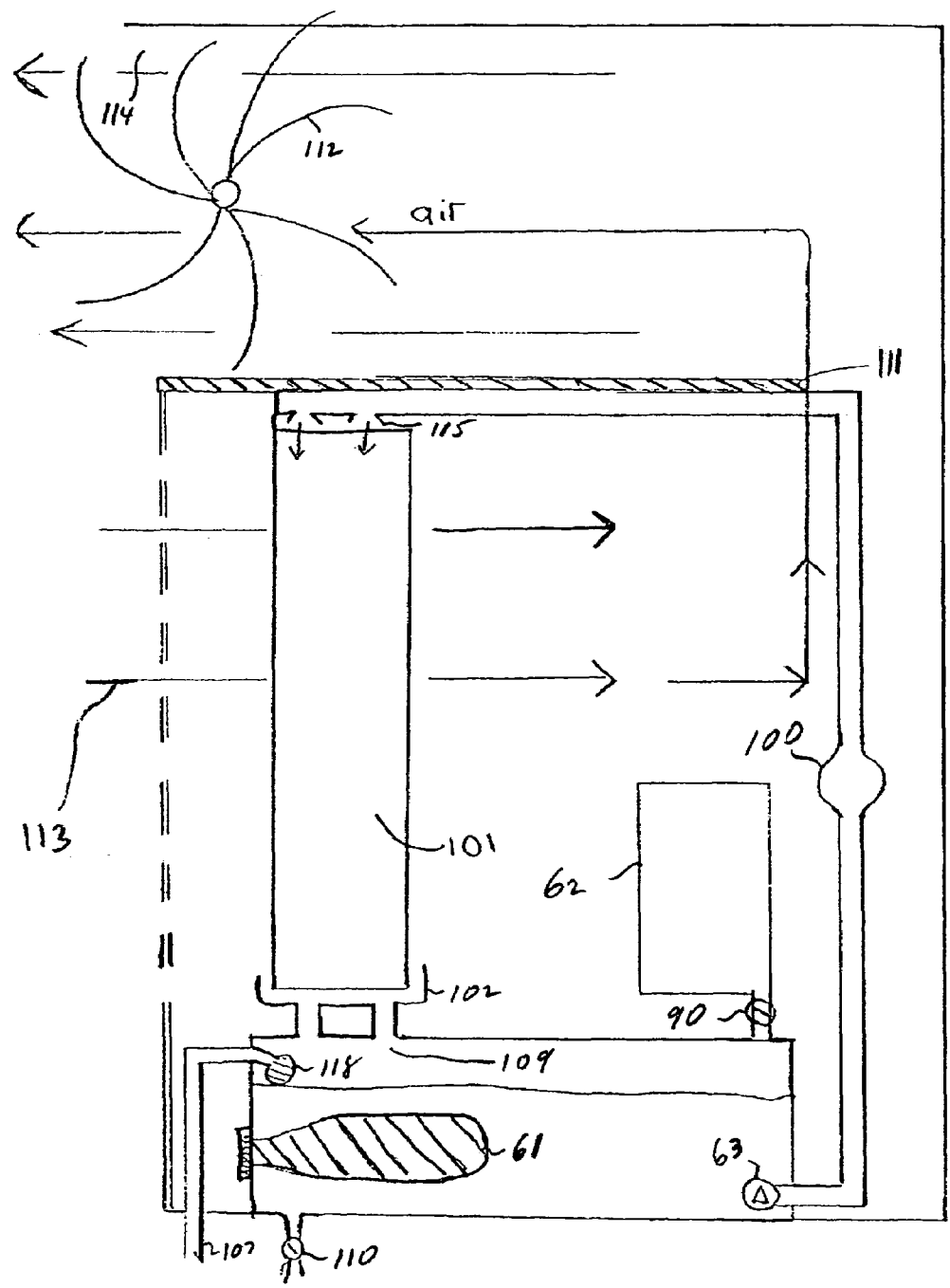

The air cleaning device (104) described in FIG. 10 can be adapted making it more practical for commercial and residential use by altering the flow direction of air as it passes through the unit. In FIG. 10, the air (116) enters on one side and the air exits (117) on the reverse side. Therefore, at least about 1 to about 2 feet must be provided for between the wall and the device (104) to provide sufficient air flow. Shown in FIG. 11 is a side view of a "wall-type" air cleaning device (120). The advantage of this device (120) is that it is space-saving and can be placed directly up against a wall or vertical barrier in an indoor room. The air enters (121) and exits (122) on the front side of the air cleaning device (120).

A different type of air moving device (112) can be utilized, such as a double inlet blower. A double inlet blower can operate much more quietly than the circular-type fan shown as an example of the air moving device (106) in FIG. 10. Using a double inlet blower, reduced decibel levels of about 40 to about 60 decibels can be achieved at air flows of around 1000 cubic feet per minute making the air cleaner more practical for commercial or residential use. Noise levels of over 60 decibels are known to be uncomfortable for most non-industrial indoor applications.

The wall-type device (120) shown in FIG. 11 operates in a similar manner to the device (104) shown in FIG. 10, except for the direction of air flow. Air (121) enters the unit at air inlet (113) and passes through the media pad (101). A barrier (111) separates the incoming (121) and outgoing (122) air streams. The double inlet blower form a stream of air though the device (120) such that the incoming air (121) flows through the media pad (101). The air then flows around the barrier (111) and exists at the air outlet (114). The semi-circular flow of air through the device (120) provides an efficient means for circulating and cleaning air in an indoor space.

The chlorine dioxide conversion efficiency (from sodium chlorite) of the air cleaning devices described above is particularly suitable for the purposes of low to moderate air flow, such as under 5,000 cubic feet per minute, but can be used for larger air flows. However, the yield of chlorine dioxide obtained from UV-mediated photolysis of sodium chlorite can be improved by shrouding the UV-bulb with a UV protective shield. The increased chlorine dioxide yield would be useful in large industrial air cleaning or air washing devices where the economics of sodium chlorite were important.

UV light decomposes both chlorite ions and chlorine dioxide (Ernst et al: Ind. Eng. Chem Res. 1994, 33, 1468-1475). The extinction coefficient for chlorine dioxide shows a minimum at 270 nm and for chlorite a maximum at around 270 nm. This means that wavelengths of over 270 nm will degrade chlorine dioxide and reduce the yield of the reaction from sodium chlorite in the chlorine dioxide generating solution.

Figure 12:
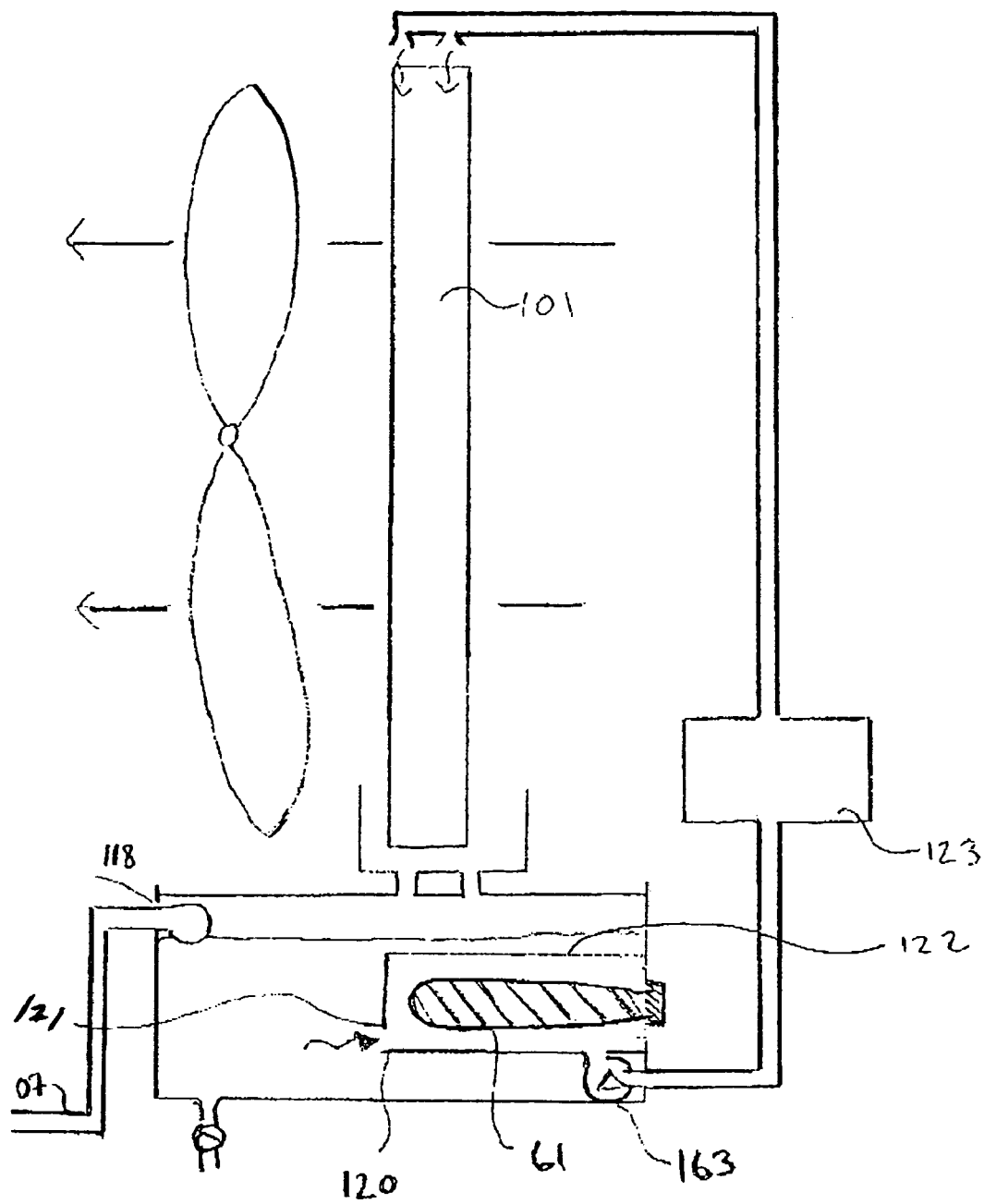

FIG. 12 shows an alternative embodiment where the UV lamp (61) is shrouded by a protective UV shield (120) in a UV-activation chamber (122). The shield may be made of any suitable material such as metal, plastic, or glass. It can also be coated with a reflective material on its interior to reduce the absorption of UV light by the shield. An aperture (121) allows the circulating solution to flow into the UV-activation chamber (122). A circulation pump (163) pulls the chlorine dioxide generating solution through the activation chamber (122) and transfers activated solution containing chlorine dioxide from the activation chamber (122) to the media pad (101). Water lost to evaporation is replaced through a float valve (107) similar to as described in earlier embodiments.

This alternative allows only a fraction of the chlorine dioxide generating solution to be exposed to the UV light source (61). The primary conversion of sodium chlorite solution (when used) to chlorine dioxide is occurring at or very near the surface of the UV lamp. Reducing the exposure of UV light to the main body of chlorine dioxide generating solution in this manner does not significantly reduce the amount of unreacted chlorite ions available for chlorine dioxide conversion.

Another important aspect of the current embodiment is the addition of an alternative chlorine dioxide generating solid dispensing device (123). In certain cases, it may be inconvenient to utilize a liquid chlorine dioxide generating solution. There are a number of reasons for this such as limitations on solution strength (generally 30% due to precipitation at lower temperatures), unfavorable shipping economics, high cost of liquid dispensing devices, etc.

The prior art describes a number of ways of dispensing and dispersing solids into liquids. Examples include solid tablet feeders, solid-concentrate cartridge dissolving feeders, flow able powder feeders, and the like. Solid tablet feeders are well known to those skilled in the art. They have been employed in water and wastewater treatment, swimming pools and hot tubs. A relatively new solid dispensing technology, known as "Solid Concentrates", has recently become available for water treatment in cooling tower, boilers, etc. "Solid Concentrate" dissolving feeders are commercially available from AP Tech Group, Inc and Safe Solid Solutions, Inc., and are suitable for use herein. Those skilled in the art will easily be able to formulate the sodium chloride generating solution into a solid form for use in the solid dispenser (123).

Figure 13:
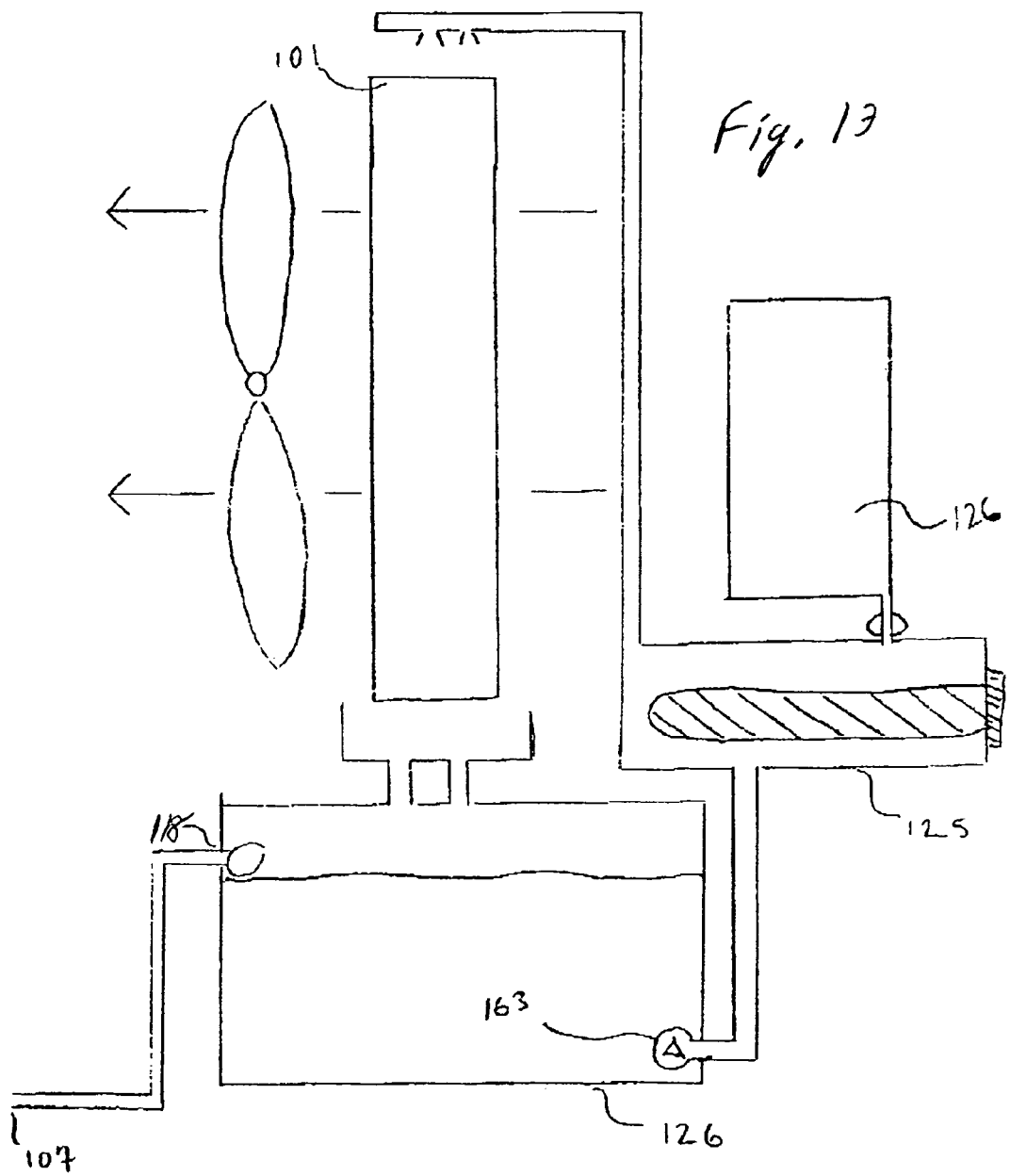
FIG. 13 illustrates an air cleanser according to the present invention.

FIG. 13 shows an alternative configuration where a UV activation chamber (125) is located outside of a main circulating tank (126). This alternative allows for equipping existing evaporative coolers with the chlorine dioxide generating apparatus of the current invention. In existing evaporative cooling units, it may not be practical to install the UV lamps in their circulation tanks or economical to replace the existing tanks.

However, these existing devices may nevertheless be installed with the UV chlorine dioxide generating apparatus by locating the UV activation chamber (125) and chlorine dioxide generating solution tank (126) separate but in communication with the existing circulation system. Additionally as described in FIG. 12, the solid dispensing system (123) can also be utilized instead of the tank (126). Another unexpected benefit of locating the activation chamber (125) outside of the main circulation tank (126) is that the UV shielding effect discussed above is also accomplished.

In certain applications of the current invention it may be necessary to "polish" the outgoing air stream. In conditions that require high concentrations of chlorine dioxide in the circulating solution, such as greater than 5 ppm, an unacceptable level of the chlorine dioxide gas may be present in the air, such as greater than 0.1 ppm, as it exits the air cleaning unit. In this regard, FIGS. 14 and 15 show an alternative embodiment of the current invention that utilizes an additional media pad (130) to absorb or neutralize residual chlorine dioxide gas as it exits the air cleaning unit.

Figure 14:
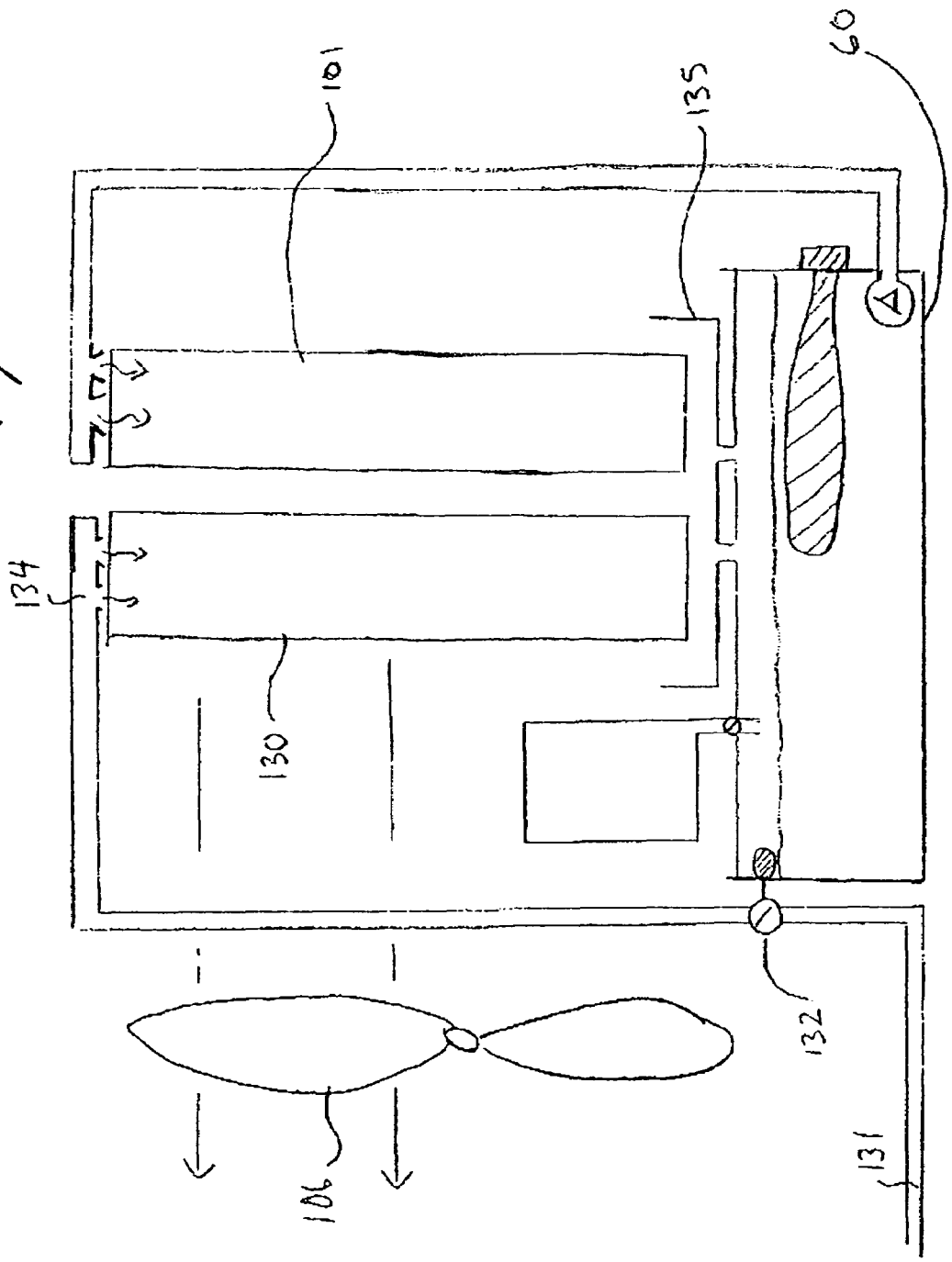
FIG. 14 illustrates an air cleanser according to the present invention.
Figure 15:
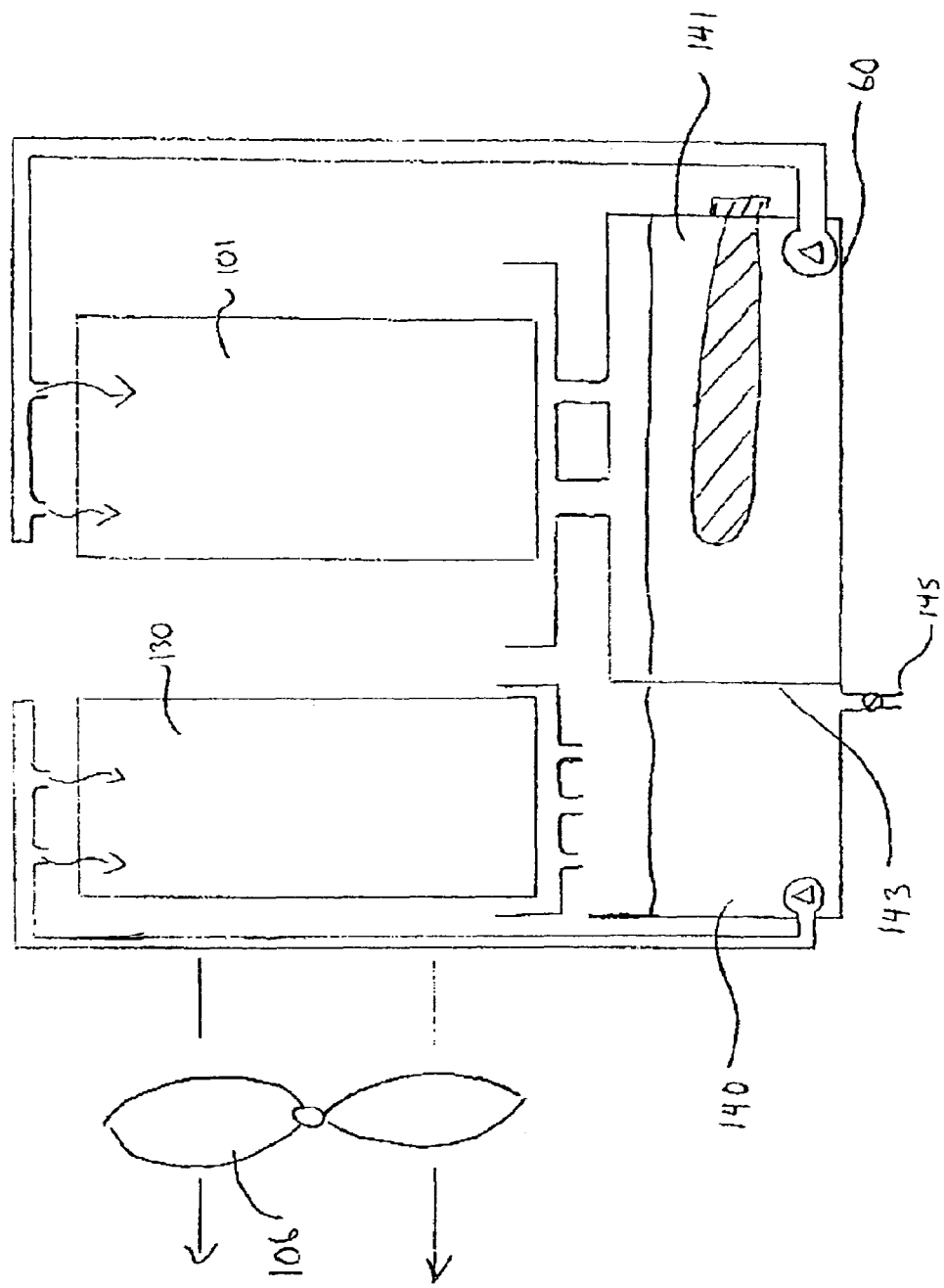
FIG. 15 illustrates an air cleanser according to the present invention.

As shown in FIG. 14, air flows through the primary media pad (101) and then through the secondary media pad (130) using the air moving device (106). The top of the secondary media pad (130) is fed with water from an outside water source. The flow of water is controlled by a float valve (132) in similar fashion to that described in earlier embodiments. The level of water in the circulating tank (160) preferably remains substantially constant through the operation of the unit.

Water will be carried away in the form of water vapor as air flows through each of the media pads (101, 130). This will in turn will cause a lowering of the water level in the tank, which will cause more water to be dispersed through the dispersion structure (134) located at the top of the secondary media pad (130).

Chlorine dioxide is readily soluble in water and will quickly dissolve in the water flowing through the secondary media pad (130). The dissolved chlorine dioxide will then flow into the drip pan (135) and be mixed with the main body of the circulating solution in the vessel (60).

FIG. 15 describes a more aggressive "polishing" method employing a chlorine dioxide neutralizing solution (140). The neutralizing solution (140) is separated from the main body of the circulating solution by a barrier (141) installed in the vessel (60). The neutralizing solution (140) can also be housed in a separate container as desired. An external water line is connected by way of float valve switch to replace water lost to evaporation in the same manner as described herein above.

A number of chemistries can be utilized in the chlorine dioxide neutralizing solution (140) such as sodium thiosulphate, sodium bisulphite, sodium sulphite, "White Liquor"-sodium hydroxide and sodium sulfite mixture, etc. Sodium thiosulfate is preferred because it reacts quickly with chlorine dioxide, is non-hazardous, can be highly concentrated in aqueous solution, and is stable for long periods.

The neutralizing solution (140) will require periodic replacement. The chlorine dioxide neutralizing compound can be added as a solid or aqueous solution during a regular unit maintenance cycle. The spent neutralizing solution can be emptied through a drain valve (145).

Figure 16:
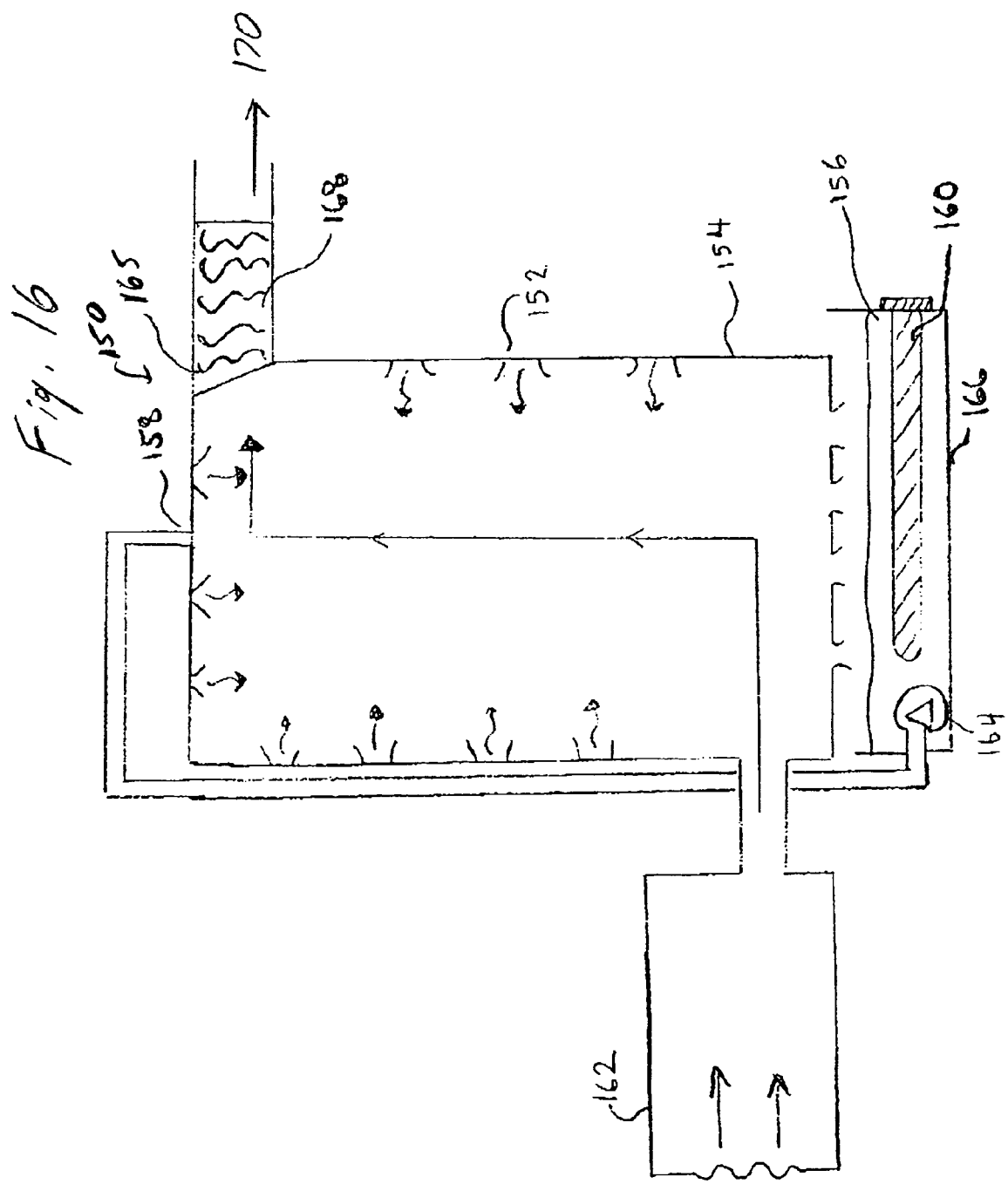
FIG. 16 illustrates an air cleanser according to the present invention.

FIG. 16 shows an industrial air washing unit (150). This unit (150) is adequate for higher air flows, such as greater than 10,000 cfm, than can efficiently be pulled through a media pad. The air washer is similar to that represented in FIG. 8, except that the current design does not employ a packed tower as does FIG. 8. The current embodiment relies on a water curtain that the air passes through. The water curtain can comprise, for example, a plurality of dispersion nozzles (152) strategically placed throughout a spray chamber (154). The dispersion nozzles conduct pressurized circulating solution, usually greater than 1000 psi, and disperse the circulating solution into small particles, usually less than 50 microns. The nozzles are commercially available and commonly known as high pressure misting or fogging nozzles.

The small particles created by atomization through the dispersion nozzles give rise to an increase in the available surface area for contact with the air stream. This allows for greater contact and hence higher efficiency for "washing" the incoming air.

The spray nozzles are fed by a distribution system (158) for the re-circulating chlorine dioxide generating solution (156) located at the top of the spray chamber (154). A high pressure pump (164) pressurizes and conducts the circulating solution to the distribution system (158). Water lost through evaporation is fed into the circulating solution tank (166) by an external water line in a similar manner as shown herein above.

The chlorine dioxide can be produced as in earlier embodiments with an ultra violet bulb (160) fed by a chlorine dioxide generating solution tank (not shown). The chlorine dioxide can also be produced by other conventional means such as through the use of a chlorine dioxide generator, although this arrangement is not preferred.

The air handling unit or blower (162) is shown at right and flows air into the spray chamber. The air flows upwards and contacts the atomized chlorine dioxide solution for the goal of sterilization, humidification, dust, and/or odor removal, as desired. The presence of dissolved chlorine dioxide gas in the circulating solution prevents common problems associated with microbiological contamination that commonly occurs in industrial air washing units.

Air exits the spray tower at an air exit (165) and is conducted through a mist eliminator pad (168) or such device to remove small droplets of solution from the exiting air flow (170).

The UV-generated chlorine dioxide system in the current invention and accompanying embodiments, FIGS. 8-16, demonstrates useful and practical applications in re-circulating air treatment systems. This system can be employed into new and existing evaporative coolers, air washers, and gas scrubbing units. These devices can easily be adapted or fitted with the chlorine dioxide UV-generating capability of the current invention as described herein. Devices that operate by treating or exposing air to a circulating fluid such as water, aqueous solutions, solvents, or absorption agents, are especially suited to benefit from the decontamination and disinfection properties of chlorine dioxide.

The physical properties of chlorine dioxide are ideal for disinfection of circulating water systems that harness exposure to air for humidification, evaporation, gas scrubbing, and air cooling. Chlorine dioxide is readily soluble as a dissolved gas and its solubility is temperature dependant. Chlorine dioxide is present as a true gas and does not form ions.

The partition coefficient or the ratio between the concentration of chlorine dioxide in the aqueous and gaseous phase can be described as: $L=(ClO_2)aqueous/(ClO_2)gaseous$. Log L varies linearly as a function of $1/T$ (W. J. Masschelein; Chlorine Dioxide, Ann Arbor Science, 1979; ISBN 0-250-40224-6).

The partition coefficient between $ClO_2$ (aqueous) and $ClO_2$ (gas) is 45 at 15° C., 38 at 22° C., and 26.5 at 35° C. This means that the concentration of chlorine dioxide in the aqueous phase is 45 times greater at 15° C. and 26.5 times greater at 35° C. than in the gaseous phase.

For example, the theoretical maximum concentration of chlorine dioxide (gas) emitted from an evaporative cooler with a two part per million circulating concentration of chlorine dioxide (aqueous) operating at 22° C. is:

$ClO_2(aq)/ClO_2(g)=38$ $ClO_2(g)=2/38=0.0526$ ppm

This value represents the $ClO_2$ (gas) concentration if the system is at 100% equilibrium. We have found that the experimental value of the concentration in the gas phase is closer to 50% or 60% of this value or roughly 0.03 parts per million. In operating conditions of the present invention the concentration of chlorine dioxide was well below the odor threshold and could not be detected by smell. The high airflow of the device, usually greater than 1000 cfm, also ensured that the chlorine dioxide was highly diluted by thorough mixing with indoor air.

United States Federal agencies, including EPA and OSHA, have established safety guidelines of 0.1 parts per million for chlorine dioxide exposure to humans. Chlorine dioxide is a reactive compound and only exists in the environment for short periods of time as documented by the EPA. The potential for human exposure is therefore insignificant and air treatment devices incorporating low circulating concentrations of chlorine dioxide solutions may be deployed safely in industrial, commercial, and residential venues.

Unexpected advantages of the present invention include but are not limited to:

(1) Pure aqueous chlorine dioxide in solution or an air stream can be produced with no dissolved solids.
(2) Chlorine dioxide solution has a neutral pH (7).
(3) Corrosive properties of chlorine dioxide are reduced.
(4) Chlorine dioxide is rapidly transported away from reactants to minimize or obviate undesirable side reactions.
(5) A high degree of control in chlorine dioxide production is provided, with a large turndown ratio.
(6) Technical grade chlorite can be used, and highly purified chlorite not required.
(7) Pure solutions of chlorine dioxide do not undergo unwanted side reactions.
(8) A single precursor system can be used and additional reagents are not required.
(9) The cost, storage and liability of additional hazardous reagents is avoided.
(10) Complex feedback and control systems not required.
(11) Production and separation of chlorine dioxide can be conducted in single step.
(12) Gaseous or aqueous chlorine dioxide can be produced as desired on demand.
(13) The present invention allows commercially useful solutions, such as hard surface cleaning agents and sanitizers, to be produced in a single step.

The use of the ultrasonic vibrations provides the following unexpected advantages:

1) Separation of chlorine dioxide from reactants to avoid UV degradation and side reactions with spent reactants.
2) Turbulence in the chlorine dioxide generating solution since fresh sodium chlorite must constantly come into contact with the UV light. UV light does not penetrate deeply into the chlorine dioxide generating solution as the sodium chlorite strongly absorbs the UV light. Therefore turbulence is necessary to expose fresh solution for UV activation.
3) Avoids having to use an air sparge that requires an air pump or compressor, such as in U.S. Pat. No. 6,171,558 (Simpson).
4) Provides a means of separating chlorine dioxide without dilution of air.
5) Avoids using the circulating tube described in the prior art (Simpson 2001) to remove the chlorine dioxide bubbles that form on the surface of the lamp.
6) The turbulence generated by the ultrasonic vibrations prevents the formation of small micro-bubbles of chlorine dioxide on the lamp and simultaneously sweeps chlorine dioxide away from the chlorine dioxide generating solution.
7) The ultrasonic transducers also produce a fine mist (usually about one micron sized particles) of chlorine dioxide solution. This can be directly employed in some applications that require surface or air stream disinfection.

While the claimed invention has been described in detail and with reference to specific embodiments thereof, it will be apparent to one of ordinary skill in the art that various changes and modifications can be made to the claimed invention without departing from the spirit and scope thereof.

The invention claimed is:

1. A chlorine dioxide generator comprising:

a reaction vessel containing a chlorine dioxide generating solution that forms an activated solution containing chlorine dioxide upon exposure to UV light;

a source of UV light constructed and arranged to provide UV light to said reaction vessel such that when said generator is operating UV light contacts the chlorine dioxide generating solution to produce the activated solution containing chlorine dioxide;

at least one solution inlet associated with said reaction vessel constructed and arranged to allow the chlorine dioxide generating solution to flow into said reaction vessel during operation of said generator;

at least one solution outlet associated with said reaction vessel constructed and arranged to allow spent activated solution to flow out of said reaction vessel during operation of said generator;

at least one chlorine dioxide exit associated with said reaction vessel constructed and arranged to allow chlorine dioxide gas to exit said reaction vessel during operation of said generator;

a gas permeable structure constructed and arranged to allow chlorine dioxide gas to exit said reaction vessel during operation of said generator by passing through said structure and to contain the chlorine dioxide generating solution and activated solution in said reaction vessel when present in the reaction vessel;

a source of ultrasonic vibrations constructed and arranged to vibrate the activated solution and facilitate removal of chlorine dioxide from the activated solution during operation of said generator; and evacuating structure in communication with the reaction vessel to facilitate continuous evacuation of chlorine dioxide from said reaction vessel during operation of said generator.

2. A chlorine dioxide generator according to claim 1, wherein said evacuating structure comprises a water-driven venturi eductor in communication with the chlorine dioxide exit and gas permeable structure which during operation of said generator the eductor provides an aqueous flow line and a reduced pressure in the reaction vessel to facilitate removal of free chlorine dioxide from the reaction vessel into an aqueous flow line forming an aqueous solution of chlorine dioxide.

3. A chlorine dioxide generator according to claim 1, wherein said evacuating structure comprises a fan in communication with the chlorine dioxide exit and gas permeable structure to facilitate removal of free chlorine dioxide from the reaction vessel into air flow forming a dilute mixture of chlorine dioxide and air during operation of said generator.

4. A chlorine dioxide generator according to claim 1, wherein said source of UV light is disposed within said reaction vessel.

5. A chlorine dioxide generator according to claim 1, wherein said source of UV light comprises at least one cylindrical UV bulb disposed within said reaction vessel.

6. A chlorine dioxide generator according to claim 1, wherein said source of UV light is external to said reaction vessel and said reaction vessel being at least partially constructed of a material that allows UV light to penetrate and contact the chlorine dioxide generating solution when present within the reaction vessel.

7. A chlorine dioxide generator according to claim 1, further comprising a metering pump connected to said solution inlet for controlling the flow of chlorine dioxide generation solution into said reaction vessel during operation of said generator.

8. A chlorine dioxide generator according to claim 1, further comprising a solenoid valve and float switch to control the flow of spent chlorine dioxide generating solution from said reaction vessel during operation of said generator.

9. A chlorine dioxide generator according to claim 1, wherein said source of ultrasonic vibrations comprises at least one ultrasonic piezoelectric plate disposed within said generator.

10. A chlorine dioxide generator comprising:

a reaction vessel containing a chlorine dioxide generating solution that forms an activated solution containing chlorine dioxide upon exposure to UV light;

a source of UV light constructed and arranged to provide UV light to said reaction vessel such that when said generator is operating UV light contacts the chlorine dioxide generating solution to produce the activated solution containing chlorine dioxide;

at least one solution inlet associated with said reaction vessel constructed and arranged to allow chlorine dioxide generating solution to flow into said reaction vessel during operation of said generator;

at least one solution outlet associated with said reaction vessel constructed and arranged to allow spent activated solution to flow out of said reaction vessel during operation of said generator;

at least one chlorine dioxide exit associated with said reaction vessel constructed and arranged to allow chlorine dioxide gas to exit said reaction vessel during operation of said generator;

a source of ultrasonic vibrations constructed and arranged to vibrate the activated solution and facilitate removal of chlorine dioxide from the activated solution during operation of said generator; and a source of air flow in communication with the reaction vessel to facilitate continuous evacuation of chlorine dioxide from said reaction vessel during operation of said generator.

* * * * *